(12) United States Patent
Tanimura et al.

(10) Patent No.: US 6,389,876 B1
(45) Date of Patent: May 21, 2002

(54) MATERIAL TESTING MACHINE, TEST PIECE ATTACHMENT SET FOR THE MATERIAL TESTING MACHINE, AND METHOD OF CONDUCTING A MATERIAL TEST WITH THE MATERIAL TESTING MACHINE

(75) Inventors: Shinji Tanimura, Osaka; Susumu Takada; Rongsheng Yin, both of Saitama, all of (JP)

(73) Assignees: Kabushiki Kaisha Saginomiya Seisakusho, Tokyo; Shinji Tanimura, Osaka, both of (JP)

( * ) Notice: Subject to any disclaimer, the term of this patent is extended or adjusted under 35 U.S.C. 154(b) by 0 days.

(21) Appl. No.: 09/595,174

(22) Filed: Jun. 16, 2000

(30) Foreign Application Priority Data

Jun. 18, 1999 (JP) .............................. 11-172583
Jun. 14, 2000 (JP) ....................... 2000-178074

(51) Int. Cl.[7] ................................ G01M 7/00
(52) U.S. Cl. .................. 73/12.01; 73/12.04; 73/12.09
(58) Field of Search .................. 73/774, 789, 790, 73/794, 12.01, 12.04, 12.09

(56) References Cited

U.S. PATENT DOCUMENTS

| | | | | |
|---|---|---|---|---|
| 4,478,086 A | * | 10/1984 | Gram | .......................... 73/781 |
| 4,603,588 A | * | 8/1986 | Niermann et al. | ............ 73/794 |
| 5,005,424 A | * | 4/1991 | Markowski | ................... 73/834 |
| 5,448,168 A | * | 9/1995 | Hirano et al. | ................ 324/209 |
| 6,089,101 A | * | 7/2000 | Ishii et al. | ..................... 73/798 |
| 6,171,812 B1 | * | 1/2001 | Smith et al. | ............. 435/40.52 |

OTHER PUBLICATIONS

No. 93–0039—Improvement of an Apparatus for Measuring Impulsive Force Generated at a Cotact Part in Collision and its Application—Yoshitake Chuman, kazuhiko Kotoh, Koichi Kaizu and Shinji Tanimura.

* cited by examiner

Primary Examiner—Benjamin R. Fuller
Assistant Examiner—Andre Allen
(74) Attorney, Agent, or Firm—McDermott, Will & Emery

(57) ABSTRACT

A material testing machine has a movable, load applying block and a fixed, load sensing block. The load sensing block has a body with sufficient volume and mass and a small sensing projection provided on the body. The sensing projection is much smaller than the body and has a side surface on which strain gages are affixed. A test piece is installed to the material sensing projection such that any load applied to the test piece may be transmitted to the sensing projection to cause a corresponding strain of the sensing projection. Any strain of the sensing projection, which may be either static strain or dynamic strain, can be determined from the outputs of the strain gages. The determined strain of the sensing projection is used to derive the load transmitted to the sensing projection and thus the load applied to the test piece.

55 Claims, 12 Drawing Sheets

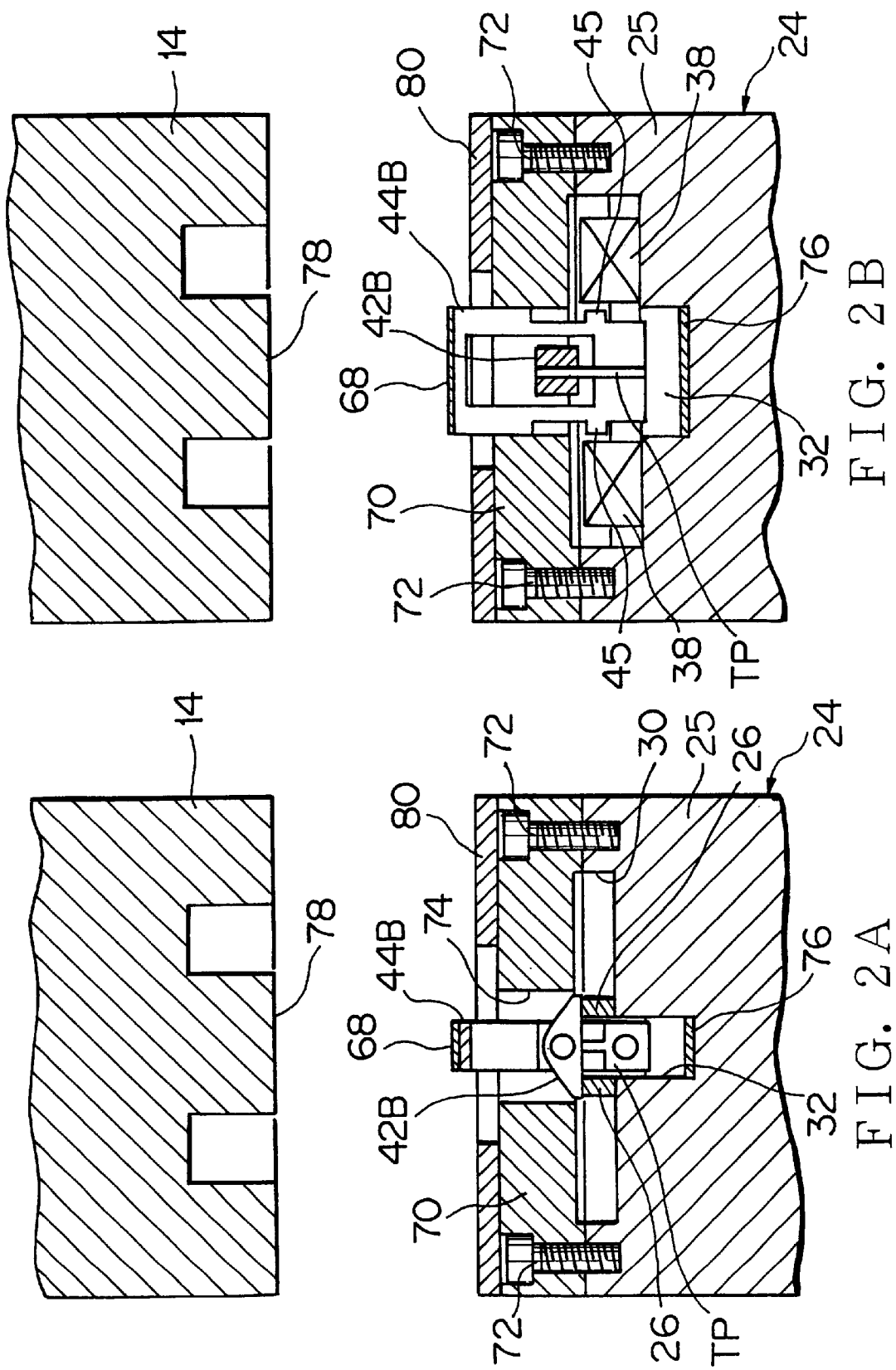

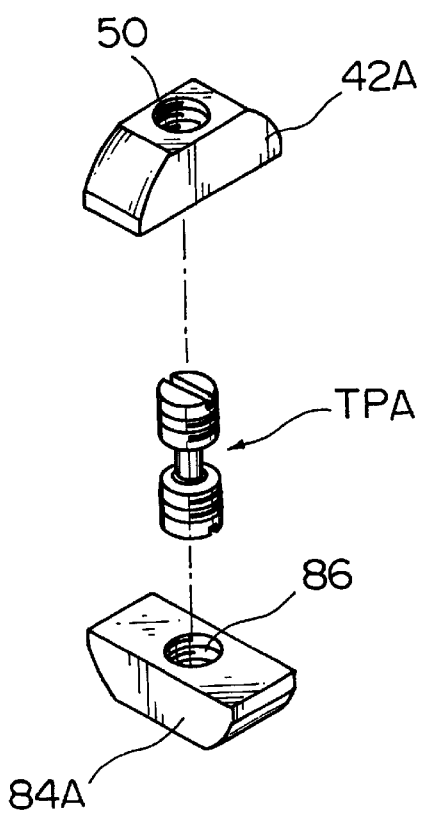
FIG. 7
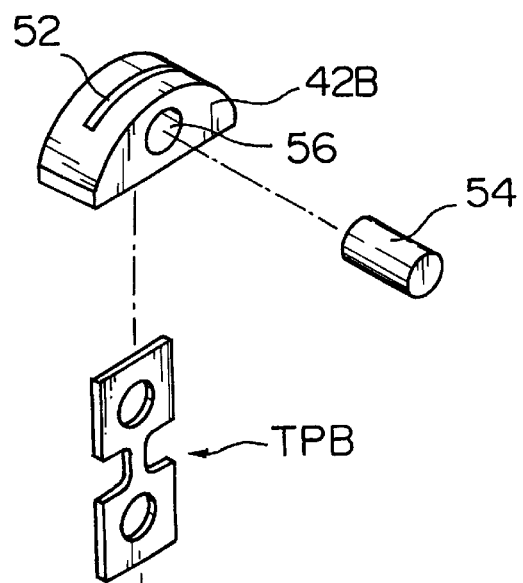
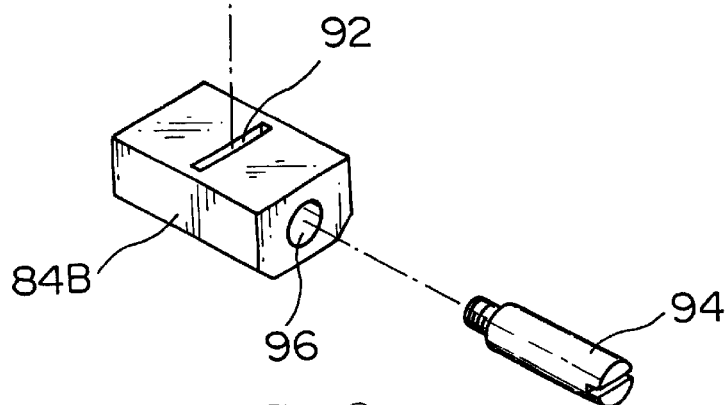
FIG. 8

MATERIAL TESTING MACHINE, TEST PIECE ATTACHMENT SET FOR THE MATERIAL TESTING MACHINE, AND METHOD OF CONDUCTING A MATERIAL TEST WITH THE MATERIAL TESTING MACHINE

BACKGROUND OF THE INVENTION

1. Field of the Invention

The present invention generally relates to materials testing and, in particular, to material testing machines, test piece attachments used with the material testing machines and methods for conducting material tests with the material testing machines.

2. Description of the Related Art

There have been proposed and utilized various material testing methods for obtaining values of parameters characterizing different materials. Many material tests are conducted by applying a load to a test piece. In some material testing methods, a test piece is subjected to a static or quasi-static load, and the resultant strain of the test piece is measured to obtain a stress-strain relationship for the material. In some other material testing methods, an increasing load is applied to a test piece until it fractures, so as to determine the stress acting on the test piece at the fracture. There are still other material testing methods for various purposes. In any case, it is highly important to obtain exact values of the loads actually applied to the test pieces.

Most material testing machines include a load measuring means for determining the actual load acting on the test piece. There are proposed many types of load measuring means, among which a suitable one meeting the requirements and purposes of a particular material testing machine is selected and used in that material testing machine. The requirements depend in part on the material testing methods to be conducted with the machine. Material testing methods may be categorized, in terms of the load to be applied to the test piece, into tensile test, compression test, torsion test, shearing test, bending test and others. Material testing methods may be also categorized, in terms of the strain rate of the test piece to be produced, into high-strain-rate test, moderate-strain-rate test and low-strain rate test. Those material tests which are conducted at high strain rates may be also called impact tests.

For purposes of ensuring safety of buildings and other structures against collapse, protecting passengers of automobiles safe at collision, or achieving appropriate numerical simulations of working and/or forming processes of metal parts at actual deformation rates, it becomes more and more important to determine characteristics of materials when they are subjected to deformation occurring at different strain rates in a wide strain-rate range covering from relatively low strain rates to relatively high strain rates. Accordingly, there have been strong needs for material testing machines and material testing methods, in which material tests may be conducted at different strain rates in a wide strain-rate range, and in which, in particular, those of tensile tests which necessitate relatively large deformation of the test piece and require relatively high strain rate higher than $10^3$/sec. may be conducted with only a low level of noise found in the measured load waveform. So far, any tensile tests conducted at strain rates higher than $10^3$/sec. have been typically subjected to a relatively high level of noise in the measured load waveform.

With the difficulties in obtaining precision measurements of material tests conducted at relatively high strain rates, measurements of material tests conducted at relatively low strain rates have been commonly used as approximations of the actually required measurements, which have been, however, often only insufficient approximations. In contrast, by utilizing the present invention, one can obtain, with ease, precision measurements of material tests conducted at different strain rates in a wide strain-rate range including relatively high strain rates corresponding to the deformation rates frequently found in an actual environment. The availability of such measurements is highly useful for many applications. For example, it may be useful in development of durable materials for structural components and automobile's parts and components. It may be also useful in improvement of accuracy in various numerical simulations for determining the behavior of a designed structure or determining the mechanisms of forming and/or working processes which produces deformation of materials occurring at different strain rates in a wide strain-rate range.

In order to cause a test piece to produce a strain at a high strain rate, an impact load is applied to the test piece. A material testing machine including load applying means for applying an impact load to a test piece may typically also include load measuring means for measuring an impact load actually applied to the test piece.

There are proposed several load measuring methods for measuring an impact load actually applied to a test piece, among which Hopkinson bar method is commonly known and accepted. The original Hopkinson bar method has been modified in various ways into a range of variations of the Hopkinson bar method, some of which are used for conducting compression test, others are used for conducting tensile test, shearing test or other material tests.

Briefly, Hopkinson bar method uses one or two elongated bars (often called the Hopkinson bar) made of a strong and resilient material such as steel. A test piece is installed to one end surface of the single bar, or between the end surfaces of the two bars facing each other. When an impact load is applied to the test piece, a stress wave is produced at the end of the bar and propagates along the longitudinal axis of the bar toward the other end. The propagating stress wave produces a corresponding dynamic strain of the bar. Strain gages are affixed on the side surface of the bar, near the end of the bar to which the test piece is installed, in order to sense any dynamic strain of the bar. The sensed dynamic strain is used to determine the dynamic stress of the bar, which in turn is used to determine the dynamic load applied to the bar. The dynamic load applied to the bar corresponds to the dynamic load actually applied to the test piece.

From the dynamic load to the test piece thus determined, the dynamic stress of the test piece can be determined. Another means is used to determine the dynamic strain of the test piece. Then, the dynamic stress and the dynamic strain of the test piece are analyzed to determine characteristics of the material of the test piece.

The stress wave propagating from the first end (to which the test piece is installed) to the second end of the bar will be reflected by the second end to return back to the first end. The reflection would provide severe noise and disturbance to the measured load waveform if the measurement is not completed before the reflection reaches the strain gages. Thus, if one wishes to apply an impact load (or a load pulse) of relatively long duration to the test piece, the Hopkinson bar has to be long enough to provide a sufficiently long turnaround time of the stress wave propagating in the bar. Otherwise, the load measurement will be practically impossible due to the reflection of the stress wave. Indeed, for allowing use of a load pulse of significantly long duration, the bar may possibly have to be as long as ten meters or more. This leads to one of drawbacks of Hopkinson bar method that a material testing machine adopting Hopkinson bar method tends to occupy an extraordinary space. Further, for such a long bar, it is practically difficult to make precision calibration of the outputs of the strain gages with reference to the magnitude of the dynamic load (impact load) actually acting on the bar.

More recently, as an attempt to overcome the drawbacks of Hopkinson bar method described above, there has been developed another method for measuring dynamic load actually acting on a test piece, which uses, in place of a Hopkinson bar, a block of steel having a small projection. Examples of devices and methods using such a steel block are taught by Yoshitake CHUMAN, Kazuhiko KOTOH, Koichi KAIZU and Shinji TANIMURA in an article "Improvement of an Apparatus for Measuring Impulsive Force Generated at a Contact Part in Collision and its Application", Transactions of the Japan Society of Mechanical Engineers, Vol. 59, No. 568, A, pages 139–144 (Article No. 93-0039) (December. 1993). In the article, the steel block used for measuring dynamic load is referred to as the stress sensing block.

The article describes that the stress sensing block is a steel block, which has a body with sufficient volume and mass and a small, cylindrical projection (called the "sensing projection") provided on the top of the body and having a longitudinal axis extending in vertical direction. The sensing projection is much smaller than the body and has strain gages affixed on its side surface. A test piece is placed on the distal (upper) end of the sensing projection. When a downward impact load is applied to the test piece from a hammer or striker, the impact load is transmitted to the distal end of the sensing projection to produce a stress wave there. The stress wave produced at the distal end of the sensing projection propagates to its proximal end and thence into the body of the stress sensing block.

The propagating stress wave produces a corresponding dynamic strain of the sensing projection, which is sensed by means of the strain gages affixed on the side surface of the projection. The outputs of the strain gages are processed to determine the dynamic stress produced in the sensing projection, from which the impact load applied to the test piece is obtained. Because only a small portion of the energy of the stress wave propagated into the body may enter again into the sensing projection to return to the strain gages, the impact load measurement is not severely affected by the reflections of the stress wave even when an impact load of relatively long duration is applied to the test piece.

By using the stress sensing block in place of a long Hopkinson bar, a more compact material testing machine may be designed, so as to eliminate the shortcomings of the Hopkinson bar method described above. The article also reports that the stress sensing block may provide good measurement accuracy.

While a material testing machine using such stress sensing block may provide good results in impact compression tests, it is still subject to certain drawbacks in impact tensile tests, in which an impact tensile load is applied to the test piece to produce a tensile strain of the test piece at a high strain rate. That is, the stress sensing block described in the article requires complicated test piece attachments in order to conduct a tensile test. It is difficult to ensure a sufficiently long stroke of the hammer or striker for striking the test piece installed on the stress sensing block so as to apply an impact tensile load to the test piece. Further, the stress sensing block does not allow the use of such test piece attachments that may effectively preventing noise and disturbance to the load measurements.

SUMMARY OF THE INVENTION

In view of the foregoing, it is an object of the present invention to provide a material testing machine which is usable for material tests conducted at different strain rates in a wide strain-rate range covering from relatively low strain rates to relatively high strain rates, as well as for material tests necessitating relatively large deformation of the test piece. The material testing machine should also provide load measurements that contain only a low level of noise even in a high-strain-rate material test conducted at a strain rate of $10^3$/sec. or higher, as well as provide precision measurements throughout the duration of an impact load including the initial phase of the impact load, in which a high level of noise is likely to occur with conventional material testing machines. The material testing machine should be also usable for material tests using various test pieces differing in geometry, such as of a circular-rod-type and a flat-strip-type. The material testing machine should be also usable, with or without a test piece attachment or a set of test piece attachments if appropriate, for a variety of material tests including compression test, tensile test, shearing test, fracture toughness test and others, which may be conducted at different strain rates in a wide strain-rate range.

It is another object of the present invention to provide a test piece attachment set usable with such a material testing machine so as to improve flexibility of the machine.

It is a further object of the present invention to provide a method of conducting a material test with such a material testing machine.

In accordance with an aspect of the present invention, there is provided a material testing machine having a frame, load applying means for applying a load in a predetermined direction to a test piece and load measuring means for sensing a load applied to the test piece.

The load measuring means comprises a load sensing block having a body with sufficient volume and mass and at least one sensing projection. The sensing projection is sufficiently smaller than the body of the load sensing block. The sensing projection has a distal end, a proximal end connected to the body of the load sensing block, a longitudinal axis extending in the predetermined direction and a side surface.

The load measuring means further comprises a plurality of strain gages affixed on the side surface of the sensing projection and processing means for processing outputs of the strain gages to determine a load acting on the sensing projection.

The load sensing block is arranged such that a stress wave produced in the sensing projection by an impact acting on the distal end of the sensing projection may propagate along the longitudinal axis of the sensing projection from the distal end to the proximal end and that a first part of the energy of the stress wave reaching the proximal end may further propagate into the body of the load sensing block to reach peripheral surfaces of the body and reflect again and again from one peripheral surface to another so that the stress wave in the body will finally decades out to lose dynamic behavior thereof.

The load sensing block is arranged such that a second part of the energy of the stress wave reaching the proximal end may be reflected at the proximal end to return back to the distal end to create shuttling echoes of the stress wave between the distal and proximal ends and that the sensing projection has a sufficiently short length so that the shuttling echoes may have a turnaround time sufficiently shorter than the duration of the impact applied to the distal end so as to prevent dynamic behavior of the sensing projection due to the stress wave from substantially effecting on the measurement provided by the load measuring means.

The load measuring means is capable of measurement of static and quasi-static loads with accuracy by using the strain gages to sense any static and quasi-static strains of the sensing projection produced by static and quasi-static loads applied to the distal end of the sensing projection and of measurement of impact loads with accuracy by using the strain gages to sense any dynamic strains of the sensing projection produced by dynamic loads applied to the distal end of the sensing projection.

The load applying means comprises a load applying block, guide means for guiding the load applying block for movement in the predetermined direction, drive means for driving the load applying block in the predetermined direction and control means for controlling the driving means.

Finally, the material testing machine is capable of installation of the test piece thereto such that any loads applied by the load applying block to the test piece may be transmitted to the distal end of the sensing projection.

The load applying block may have a body with sufficient volume and mass and at least one load applying projection projecting from the body of the load applying block. Further, the load applying block may be arranged such that a stress wave produced in the load applying projection by an impact acting thereon may propagate into the body of the load applying block to reach peripheral surfaces of the body and reflect again and again from one peripheral surface to another, so as to prevent dynamic behavior of the load applying block due to the stress wave from substantially effecting on a load applied to the test piece.

In one embodiment of the material testing machine, the predetermined direction is vertical direction and the load applying block is disposed above the load sensing block. The load sensing block has a top surface facing the load applying block and having a pair of the sensing projections formed thereon. The load sensing block has a receptacle formed in the top surface between the pair of sensing projections, for receiving the test piece having test piece attachments connected thereto. Finally, the pair of sensing projections are capable of placement thereon of a first test piece attachment connected to the test piece for installation of the test piece to the material testing machine.

In another embodiment of the material testing machine, the load sensing block has a side ridge protruding in transverse direction with respect to the predetermined direction from the body of the load sensing block. The side ridge has an end surface extending in transverse direction with respect to the predetermined direction. The load sensing block has the sensing projection provided on the end surface. Finally, the sensing projection has a connecting portion at the distal end thereof for connection with the test piece.

In accordance with another aspect of the present invention, there is provided a test piece attachment set used for installation of a test piece to a material testing machine as mentioned above, for conducting a tensile test. The test piece has first and second ends to be directed toward the load applying block and the load sensing block, respectively, when the test piece is installed to the material testing machine. The test piece attachment set comprises first and second test piece attachments for connection to the first and second end of the test piece, respectively. The first test piece attachment being adapted for placement on the distal ends of the pair of sensing projections while connected to the first end of the test piece. The second test piece attachment being adapted for engagement with the load applying block while connected to the second end of the test piece. Finally, application of a compressive load by the load applying block to the second test piece attachment results in application of a tensile load between the first and second ends of the test piece.

BRIEF DESCRIPTION OF THE DRAWINGS

The above and other objects, features and advantages of the present invention will be apparent from the following detailed description of preferred embodiments thereof, reference being made to the accompanying drawings, in which:

FIGS. 2A and 2B are cross-sectional views showing critical components of a load measuring unit and a load applying unit used in the material testing machine of FIG. 1;

FIG. 7 is a perspective view of a test piece attachment set for use with a circular-rod-type test piece in a tensile test to be conducted with the material testing machine of the second embodiment;

FIG. 8 is a perspective view of a test piece attachment set for use with a flat-strip-type test piece in a tensile test to be conducted with the material testing machine of the second embodiment;

DETAILED DESCRIPTION OF PREFERRED EMBODIMENTS

Referring now to the accompanying drawings, preferred embodiments of the present invention will be described in detail.

Figure 1:
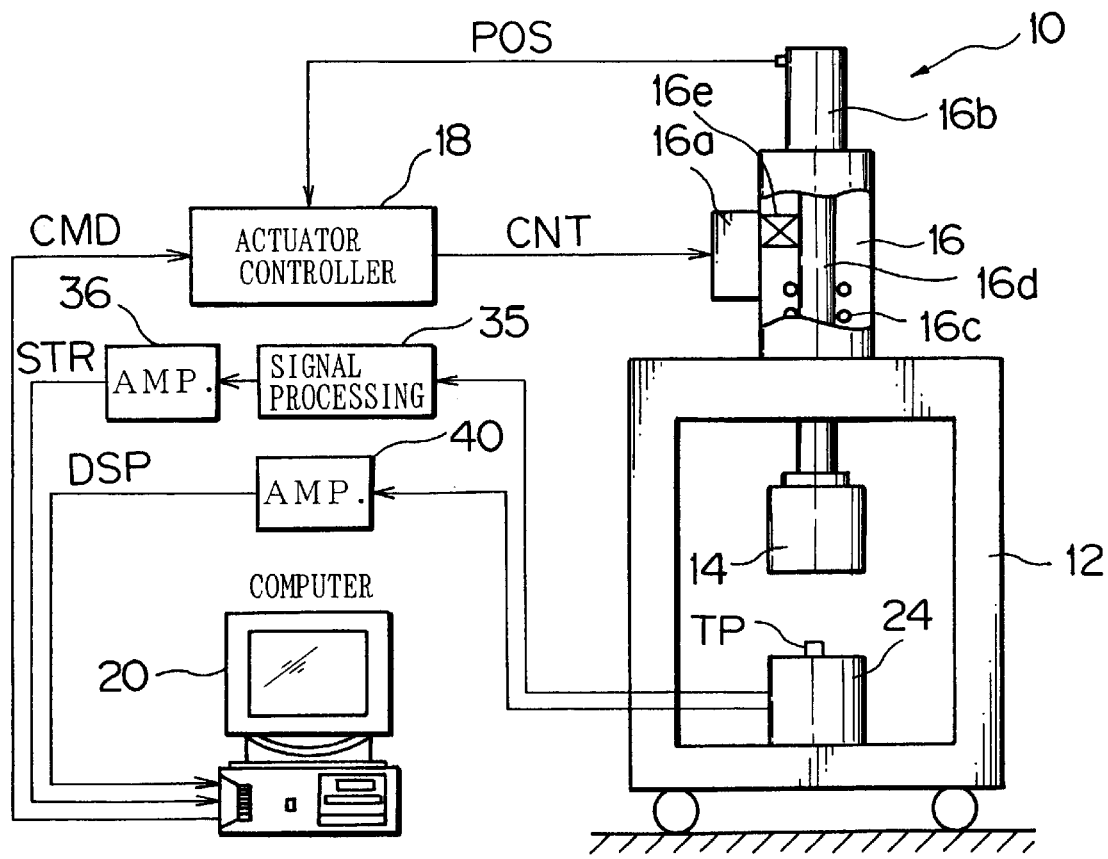
FIG. 1 is a schematic showing a material testing machine arranged and constructed in accordance with a first embodiment of the present invention.

FIG. 1 schematically shows a material testing machine 10 constructed and arranged in accordance with a first preferred embodiment of the present invention. The material testing machine 10 includes a frame 12, a load applying unit for applying a desired load to a test piece TP, a load measuring unit for measuring an actual load applied to the test piece TP and a test-piece-strain measuring unit for measuring a strain of the test piece TP produced by a load applied thereto.

The load applying unit includes a movable block 14 (referred to as the "load applying block" hereinafter), an actuator assembly 16 supported by the frame 12 for guiding and driving the load applying block 14 for vertical movement, an actuator controller 18 and a computer 20. The actuator controller 18 and the computer 20 cooperate with each other to control the actuator assembly 16.

The load applying block 14 is a block made of steel and having a volume and a mass both of which are sufficient for the purposes of the load applying block 14 describe in detail below. The load applying block 14 may be made of any other material which has sufficient toughness and strength for bearing the loads applied to the load applying block 14 during the material test conducted with the material testing machine, such as phosphor bronze.

The actuator assembly 16 is a hydraulic cylinder assembly including a piston (not shown) with a piston rod (not shown). The piston is movable in vertical direction. The actuator assembly 16 includes a control valve 16a (only schematically shown) for controlling the action of the hydraulic cylinder and a position sensor 16b for sensing the vertical position of the piston to generate position signals POS indicative of the sensed vertical position of the piston. The actuator assembly 16 further includes a ram rod 16d extending in vertical direction and supported by linear bearings 16c for vertical movement. The ram rod 16d has a lower end connected to the load applying block 16. The connection between the load applying block 16 and the ram rod 16d is not a rigid connection; any strong, upward force acting on the load applying block 14 may cause an upward displacement of the load applying block 14 relative to the ram rod 16d. Such connection may be provided by connecting these members through a lost motion connection or through a resilient interconnection member.

A clutch 16e is provided for selectively connecting the piston rod of the actuator assembly 16 to the ram rod 16d. By connecting the clutch 16e and operating the actuator assembly 16, the load applying block 14 is moved in vertical direction. The vertical position of the load applying block 14 can be determined from the position signals PS generated by the position sensor 16b. By disconnecting the clutch 16b after the load applying block 14 is lifted up to a desired vertical position, the load applying block 14 is released into a free fall. When this occurs, the load applying block 14 is accelerated by the gravity to impact either the test piece TP itself or a test piece attachment if attached to the test piece TP, so that an impact load is applied to the test piece TP. Such a impact load is used for material tests conducted to be at relatively high strain rates, such as, high-strain-rate test and ultra-high-strain-rate test (or impact test).

One or more additional weights (not shown) may be rigidly attached to the load applying block 14. The falling mass (or inertial mass) may be adjusted through appropriate selection of the additional weight(s) used. It is noted that the mass of the ram rod 16d is excluded from the inertial mass and thus does not contribute to the impact load, by virtue of the non-rigid connection between the ram rod 16d and the load applying block 14, which allows no transmission of a stress wave between them. This is important because if the load applying block 14 were rigidly connected to the ram rod 16d, a stress wave produced in the load applying block 14 by an impact could be transmitted to the ram rod 16d. Any transmitted stress wave would propagate along the longitudinal axis of the ram rod 16d to create shuttling echoes of the stress wave due to reflections of the stress wave at the opposite ends of the ram rod 16d. Since the ram rod 16d has a significant length, such shuttling echoes would have a relatively long turnaround time (or a relatively low frequency) and thus provide disturbances to the impact load actually applied by the load applying block to the test piece. In contrast, with the load applying block 14 having the structure described above, no stress wave is allowed to transmit between the ram rod 16d and the load applying block 14, to prevent creation of such shuttling echoes so as to achieve highly improved accuracy in load measurement in high-strain-rate material tests.

Thus, the falling mass contributing to the impact load to be applied to the test piece TP is essentially composed of the mass of the load applying block 14 and the mass of the additional weight(s) if any, and is adjustable by selection of the additional weight(s) used. Further, the velocity of the load applying block 14 at the time of impact may be adjustable by selecting the falling distance (i.e., the vertical displacement of the falling mass from the start point of the fall to the point of the impact). With appropriate selections of these parameters, the duration and magnitude of the impact load to be applied to the test piece TP may be adjusted, while the impact load may contain only a low level of noise even when it is of relatively long duration.

The actuator controller 18 receives command signals CMD from the computer 20 as well as position signals POS from the position sensor 16b as feedback signals. The actuator controller 18 generates control signals CNT based on the received signals in a known manner, and provides the generated control signals CNT to the control valve 16a so as to control the actuator assembly 16. The load applying block 14 may be controlled by the actuator assembly 16 such that the load applying block 14 may be (i) moved to a desired vertical position if such a position is designated by the command signals CMD, (ii) lifted up/down at a desired speed if such a speed is designated by the command signals CMD, and (iii) urged downward to impose a desired load (which may be a static or quasi-static load) if such a load is designated by the command signals CMD.

Thus, the material testing machine 10 is capable of material tests at relatively low strain-rates, in which the strain-rate is controlled by controlling the speed of operation of the actuator assembly 16 and thus the speed of the load applying block 14. The material testing machine 10 is also capable of material tests at relatively high strain-rates, such as impact tests, in which the strain speed is controlled mainly by controlling the vertical position of the load applying block 14 from which it is released into a free fall. In addition, the material testing machine 10 is capable of material tests using either static or quasi-static load, in which the load is controlled by controlling the urging force produced by the actuator assembly 16.

In operation, the human operator of the material testing machine 10 uses the computer 20 to operate the actuator assembly 16 to control the position and/or the speed of the load applying block 16. The operator may operate the material testing machine 10 to subject the load applying block 14 to a free fall from a controlled, vertical position as controlled by the actuator controller 18 and the computer 20. Thus, the actuator assembly 16 may serve both (i) as guide means for guiding the load applying block 14 for vertical movement and (ii) as drive means for driving the load applying block 14 in vertical direction. Also, the actuator controller 18 and the computer 20 together serve as control means for controlling the drive means.

The present invention is not limited to the use of the load applying unit comprising a hydraulic cylinder, such as described above. Depending on the requirements of the material tests to be conducted, any of other types of actuators, such as air cylinders and electromagnetic actuators, may be used for the load applying unit.

The load measuring unit of the material testing machine 10 comprises a fixed block 24 (referred to as the "load sensing block" hereinafter), which is rigidly supported by the frame 12 and to which the test piece TP is installed. The load sensing block 14 is a block made of steel and having a volume and a mass both of which are sufficient for the purposes of the load sensing block 24 describe in detail below. The load sensing block 24 may be made of any other material which has sufficient toughness and strength for bearing the loads applied to the load sensing block during materials testing, such as phosphor bronze. The load applying block 14 is disposed just above the load sensing block 24.

Briefly, the load sensing block 24 provides the functionality similar to that of the Hopkinson bar known in the art, i.e., it supports the test piece TP and permits measurement of an impact load applied to the test piece TP while preventing any reflected stress wave from disturbing the measured impact load waveform. The load sensing block 24, however, can be made much more compact than the Hopkinson bar for impact tests using impact loads of relatively long duration. The load sensing block 24 has a body 25 and a pair of sensing projections 26 provided on the top of the body 25. Each sensing projection 26 has a longitudinal axis extending in vertical direction, with the upper and lower ends constituting distal and proximal ends thereof, respectively. Thus, the sensing projections 26 are connected with the body 25 at their lower, proximal ends.

The load measuring unit further includes strain gages 28 (see FIG. 3) affixed on each sensing projection 26 and signal processing circuitry 35 associated with the strain gages 28 for processing output signals of the strain gages 28 to derive voltage signals STR indicative of longitudinal strains of the sensing projections 26. While the sensing projections 26 are formed in a right-circular-cylindrical shape in the embodiment, they may be also formed in a rectangular-parallelepiped shape or others as long as such shape provides no difficulty in measurement using the strain gages affixed on the sensing projections.

Figure 3:
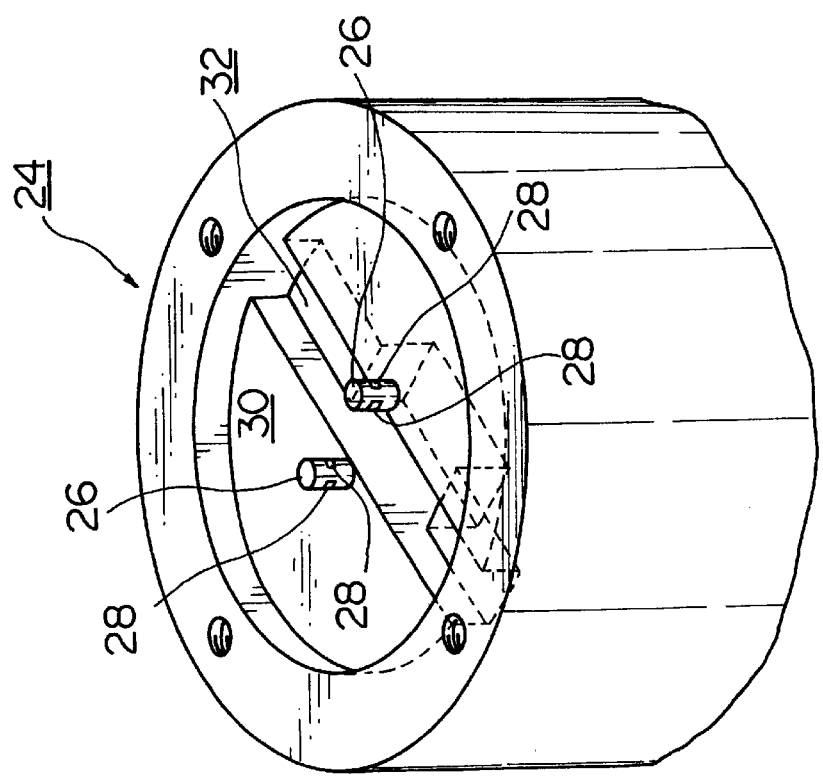
FIG. 3 is a perspective view of a part of a load sensing block used in the material testing machine of FIG. 1, showing a pair of sensing projections.

More specifically, the body 25 of the load sensing block 24 is formed generally in a right-circular-cylindrical shape with its axis extending in vertical direction. The shape of the body 25 is not limited to this, but may be of any of a variety of shapes including a box shape for example. The height and the diameter of the body 25 may be for example about 100 to 300 mm (the height is not required to be equal to the diameter). The body 25 has a top surface, in which a shallow, circular recess 30 is formed as shown in FIG. 3. The bottom of the circular recess 30 is flat and has a receptacle 32 formed therein between the pair of sensing projections 26, for receiving a test piece TP with a set of test piece attachments connected thereto.

Each sensing projection 26 is formed in a right-circular-cylindrical shape with its axis extending in vertical direction, but is much smaller than the body 25 of the load sensing block 24. The height and the diameter of the sensing projections 26 may be for example about 5 to 50 mm (the height is not required to be equal to the diameter). The sensing projections 26 are disposed at the center of the top recess 30 with a small distance between them. The sensing projections 26 may be preferably formed as integral parts of the load sensing block 24. For example, the body 25 and the sensing projections 26 may be fabricated from a single blank of steel by machining it with a milling machine, so that the body 25 and the sensing projections 26 are formed to be completely integral with each other. It is also possible to separately fabricate the body 25 and the sensing projections 26 and thereafter connects them into a unitary structure through a suitable process, such as welding; however, in such a case, careful consideration has to be made for ensuring good propagation of any stress wave from the sensing projections 26 to the body 25.

Specifically, the load sensing block 24 is arranged such that a stress wave produced in each sensing projection 26 by an impact acting on its distal end may propagate along its longitudinal axis from the distal end to the proximal end, and that a first part of the energy of the stress wave reaching the proximal end may further propagate into the body 25 to reach peripheral surfaces of the body 25 and reflect again and again from one peripheral surface to another so that the stress wave in the body 25 will finally decades out to lose dynamic behavior thereof. The cross section of the sensing projection 26 is much smaller than that of the body 25, so that only a negligible portion of the energy of the stress wave in the body 25 may enter again into the sensing projection 26. Any amount of energy entering again into the sensing projection 26 may produce the noise in the measured waveform of the dynamic load. In the above arrangement of the load sensing block 24, only a negligible potion of the energy may enter again into the sensing projection 26, so that the level of noise caused by such portion of the energy is limited, with the result that even an impulsive load of relatively long duration may be effectively measured with accuracy.

A second part, substantially equal to the remaining part, of the energy of the stress wave reaching the proximal end may be reflected at the proximal end to return back to the distal end to create shuttling echoes of the stress wave between the distal and proximal ends of the sensing projection 26. The sensing projection 26 has a sufficiently short length so that the shuttling echoes may have a turnaround time sufficiently shorter than the duration of the impact applied to the distal end, so as to prevent dynamic behavior of the sensing projection due to the stress wave from substantially effecting on the measurement provided by the load sensing unit. The shuttling echoes of such a short turnaround time have little effects on the measurements because the noise due to such shuttling echoes may be filtered out with ease. Further, the turnaround time may be preferably shorter than the time region of the leading edge of an impact load (or load pulse) acting on the sensing projection 26, so that the leading edge of the measured load pulse is free from any harmful effects of the shuttling echoes.

Each sensing projection 26 has four strain gages 28 affixed on its side surface at angular intervals of ninety degrees. The eight strain gages affixed on the pair of sensing projections 26 are connected to the associated, signal processing circuitry 35 of a known type, for monitoring variations in resistance of the strain gages 28, so as to generate signals indicative of the longitudinal strains of the sensing projections 26. The output signals from the circuitry 35 are amplified by an amplifier 36 into strain signals STR indicative of the strains of the sensing projections 26, which are read into the computer 20.

The test piece TP, when installed to the material testing machine 10, is placed on the distal ends of the sensing projections 26 either directly or through a test piece attachment connected to the test piece TP, as described later in detail. By operating load applying block 14 to apply a load to the test piece TP placed on the sensing projections 26, a corresponding longitudinal compressive load acts on each sensing projection 26 from the test piece TP, with the result that a corresponding longitudinal strain of the sensing projection 26 is produced.

The computer 20 uses the strain signals STR from the strain gages 28 to derive the longitudinal compressive loads acting on the respective sensing projections 26, and then uses the longitudinal compressive loads to determine the load applied to the test piece TP. Thus, the circuitry 35, the amplifier 36 and the computer 20 together serve as processing means for processing outputs of the strain gages 28 to determine the loads acting on the respective sensing projections 26 and thereby to determine the load applied to the test piece TP.

By virtue of the above arrangement, the load measuring unit used in the material testing machine 10 is capable of measurement of static and quasi-static loads with accuracy, by using the strain gages 28 to sense any static and quasi-static strains of the sensing projections 26 produced by static and quasi-static loads applied to the distal ends of the sensing projections 26. The load measuring unit is also capable of measurement of impact loads with accuracy, by using the strain gages 28 to sense any dynamic strains of the sensing projections 26 produced by dynamic (impact) loads applied to the distal ends of the sensing projections 26.

In other words, the load measuring unit, comprising the load sensing block 24, strain gages 28 and the processing means, can serve as a load cell to measure static and quasi-static loads, as well as serve as a sensing device mentioned above and taught by Yoshitake CHUMAN, Kazuhiko KOTOH, Koichi KAIZU and Shinji TANIMURA in an article "Improvement of an Apparatus for Measuring Impulsive Force Generated at a Contact Part in Collision and its Application", Transactions of the Japan Society of Mechanical Engineers, Vol. 59, No. 568, A, pages 139–144 (Article No. 93-0039) (December. 1993). In the article, the sensing device is referred to as the stress sensing block. Thus, the load measuring unit used with the present invention can provide the functionality of the stress sensing block described in the article, as well.

The test-piece-strain measuring unit used in the material testing machine 10 includes a pair of displacement sensors 38 (see FIG. 2B), which are disposed in the receptacle 32 formed in the body 25 of the load sensing block 24. As described, the receptacle 32 is formed in the bottom of the top recess 30 of the body 25, at the center of the recess 30, and between the sensing projections 26. Each displacement sensor 38 comprises a known combination of a magnetic scale and a magnetic head. The displacement sensors 38 serve to sense the vertical positions of a pair of side projection 45 (see FIGS. 4 and 5) formed on a test piece attachment (described later in detail) connected to the lower end of the test piece TP, so as to produce displacement signals DSP indicative of the vertical positions of the side projections 45. The displacement signals DSP from the pair of displacement sensors 38 are amplified by the amplifier 40 (see FIG. 1) and read into the computer 20. The computer 20 uses the displacement signals DSP to derive the displacement of the test piece attachment connected to the lower end of the test piece TP, and then uses the derived displacement to compute the strain of the test piece TP actually produced.

When a test piece TP is set to the material testing machine 10 for conducting a material test, the test piece TP is installed to the load sensing block 24 such that any loads applied by the load applying block 14 to the test piece TP may be transmitted to the distal ends of the sensing projections 26. For this purpose, a test piece attachment set may be used if necessary. With appropriate selection of a test piece attachment set, the material testing machine 10 may be used for different material tests (including compression test, tensile test, torsion test and others) using different test pieces (including those of circular-rod-type, flat-strip-type and others) at different strain rates in a wide strain-rate range.

Figure 5:
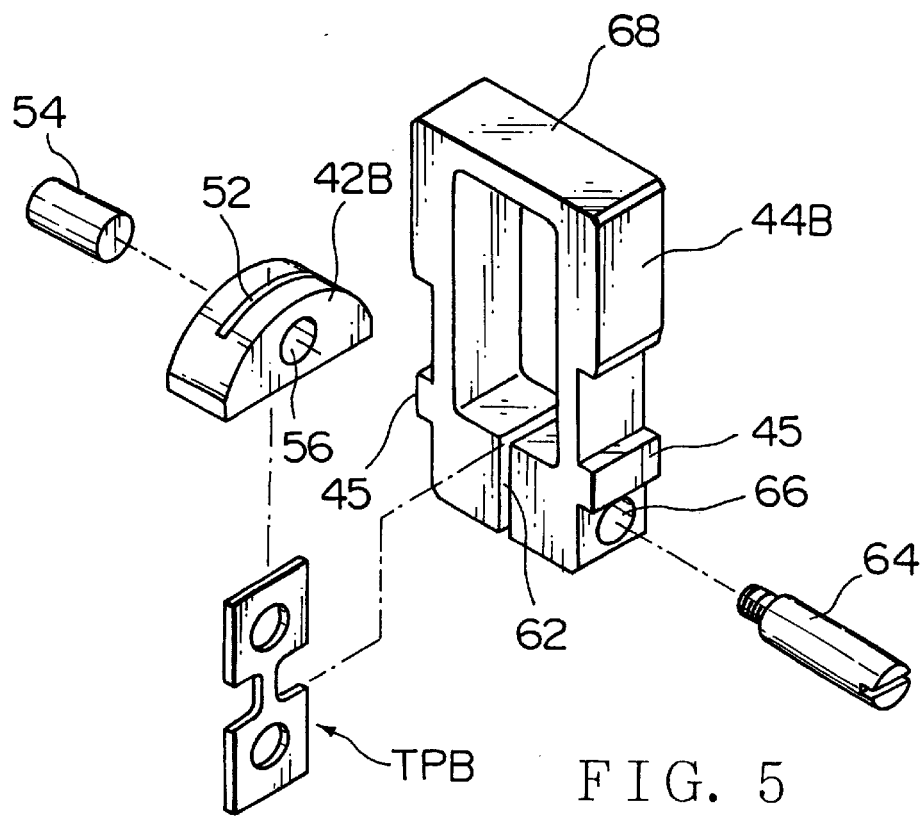
FIG. 5 is a perspective view of a test piece attachment set for use with a flat-strip-type test piece in a tensile test to be conducted with the material testing machine of FIG. 1.
Figure 4:
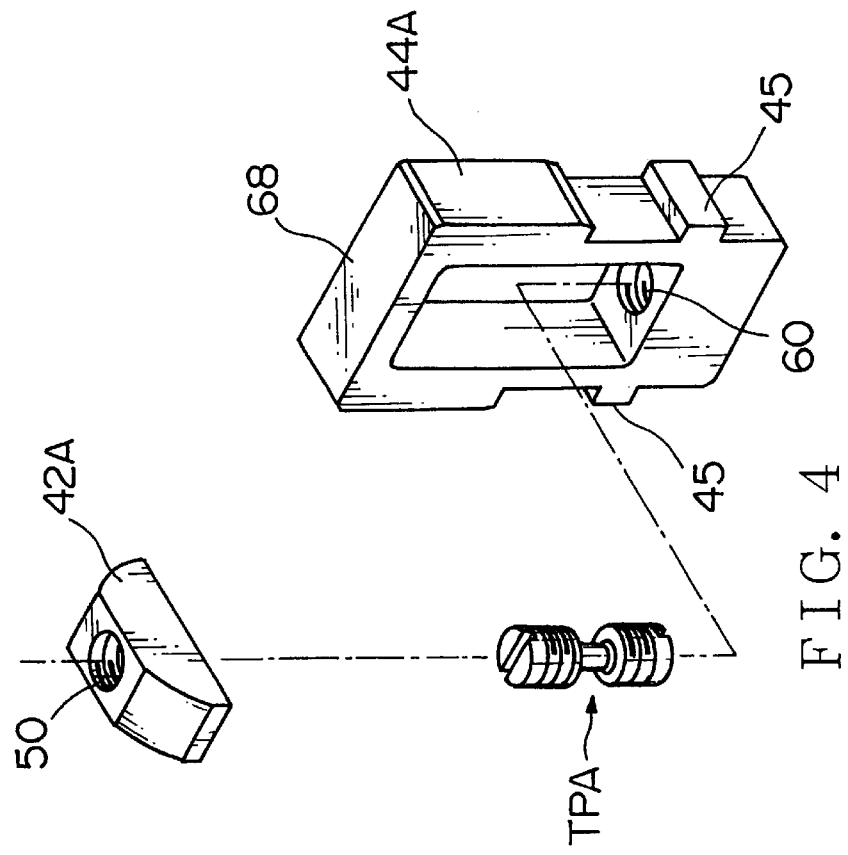
FIG. 4 is a perspective view of a test piece attachment set for use with a circular-rod-type test piece in a tensile test to be conducted with the material testing machine of FIG. 1.

Various types of test piece attachments may be used for different material tests and for different test pieces. FIGS. 4 and 5 show two examples of the test piece attachment set, which are specifically designed for tensile tests to be conducted with the material testing machine 10. The attachment set of FIG. 4, comprising first and second attachment members 42A and 44A, may be used for a tensile test using a circular-rod-type test piece TPA. The attachment set of FIG. 5, comprising first and second attachment members 42B and 44B, may be used for a tensile test using a flat-strip-type test piece TPB.

For conducting a tensile test, at first, the first attachment member (42A or 42B) and the second attachment member (44A or 44B) are connected to the upper and lower ends of the test piece (TPA or TPB), respectively, to form a test piece/attachment set assembly. The assembly is then disposed in position between the load applying block 14 and the load sensing block 24 with the first (upper) end of the test piece (TPA or TPB) being directed toward the load applying block 14 and the second (lower) end toward the load sensing block 24.

With the assembly being disposed in position, the first attachment member (42A or 42B) connected to the upper end of the test piece (TPA or TPB) is placed at its opposite ends on the distal ends of the sensing projections 26. Specifically, the first attachment member 42A of FIG. 4 is an elongated bar-like member made of steel, which extends in horizontal direction when installed to the load sensing block 14. It has a threaded hole 50 at the center thereof for receiving one of threaded ends of the circular-rod-type test piece TPA. The first attachment member 42B of FIG. 5 is also an elongated bar-like member made of steel, which extends in horizontal direction when installed to the load sensing block 14. It has a slit 52 at the center thereof for receiving one end of the flat-strip-type test piece TPB and a hole 56 for snugly receiving a pin 54 for securing the end of the test piece TPB to the first attachment member 42B.

Thus, the first attachment member (42A or 42B) is connected at the center thereof to the test piece (TPA or TPB) and placed at the opposite ends thereof on the distal (top) ends of the pair of sensing projections 26. The first attachment member (42A or 42B) has a sufficient rigidity so that when placed on the distal ends on the sensing projections 26 it provides accurate positioning of the upper end of the test piece (TPA or TPB) at a desired vertical position.

With the assembly being disposed in position, the second attachment member (44A or 44B) connected to the lower end of the test piece (TPA or TPB) is engageable with the load applying block 14 to receive a load therefrom. Specifically, the second attachment member 44A of FIG. 4 is a rectangular-ring-shaped member made of steel and having four sides; upper, lower and a pair of upright sides. The lower side has a threaded hole 60 at the center thereof for receiving the lower threaded end of the circular-rod-type test piece TPA. Similarly, the second attachment member 44B of FIG. 5 is a rectangular-ring-shaped member made of steel and having four sides; upper, lower and a pair of upright sides. The lower side has a slit 62 at the center thereof for receiving the lower end of the flat-strip-type test piece TPB and a hole 66 for snugly receiving a pin 64 for securing the lower end of the test piece TPB to the second attachment member 44B. Thus, the second attachment member (44A or 44B) has its lower side capable of connection to the test piece (TPA or TPB).

The second attachment member (44A or 44B) has a pair of side projections 45 formed on its opposite upright sides and projecting outwardly such that vertical positions of the side projections 45 may be sensed by the pair of displacement sensors 38 described above. The second attachment member (44A or 44B) has a sufficient rigidity so that sensing the vertical positions of the side projections 45 ensures measurement of vertical positions of the lower end of the test piece TPB with accuracy. The displacement sensors 38, using a combination of a magnetic scale and a magnetic head as described above, is durable and maintains its accuracy even after long-term use. Alternatively, the displacement sensors 38 may be any other type of sensors.

The load applying block 14 has a bottom surface facing to the top surface of the load sensing block 24 (see FIGS. 2A and 2B). The load applying block 14 also has a load applying area 78 defined at the center of the bottom surface. The upper side of the rectangular-ring-shaped second attachment member (44A or 44B) receives a downward load from the load applying area 78. As seen from FIGS. 4 and 5, when a downward load is applied from the load applying block 14 to the top surface of the upper side of the second attachment member (44A or 44B), the test piece (TPA or TPB) is thereby subjected to a corresponding tensile load.

The test piece attachment sets of FIGS. 4 and 5, which are specifically designed for a tensile test to be conducted with the material testing machine 10, may be used not only for those tensile tests which use static or quasi-static loads but also for those using dynamic or impact loads. In a tensile test in the latter category, the load applying block 14 will impact the top surface of the upper side of the second attachment member (44A or 44B). A cushion layer 68, which may be formed of a sheet of soft metal, of polymer, or of any suitable inorganic material, is affixed on the top surface of the upper side in order to avoid any inconveniences which could be otherwise caused by the impact. That is, the cushion layer 68 serves to prevent the load applying block 14 from snapping the second attachment member (44A or 44B) away from appropriate position at the impact. If the second attachment member (44A or 44B) is snapped away by the load applying block 14, any load measurements of good accuracy can not be expected. The cushion layer 68 affixed on the second attachment member (44A or 44B) effectively prevents such situation, so as to ensure good accuracy in load measurement.

The general geometry of the test piece/attachment set assembly shown in FIG. 4 is substantially the same as the assembly shown FIG. 5, so that these assemblies may be installed to the load sensing block 24 in the same manner. That is, while FIGS. 2A and 2B show the assembly of FIG. 5 as installed to the load sensing block 24, the assembly of FIG. 4 may be also installed to the load sensing block 24 in the same manner. In either case, when the assembly is installed to the load sensing block 24, the opposite ends of the first attachment member (42A or 42B) are placed on and supported by the distal ends of the sensing projections 26, and thereby the assembly is supported by the sensing projections 26.

The load sensing block 24 also has a guide plate 70 of a generally disk-shape fixedly attached on the top of the load sensing block 24 by means of screws 72. The guide plate 70 has a guide opening 74 of a cross-shape as viewed in plan. The guide opening 74 serves as guide means for guiding the second attachment member (44A or 44B) to allow only displacement thereof in vertical direction while substantially prevent rotation and displacement thereof along a horizontal plane, so as to constrain the second attachment member (44A or 44B) to a desired horizontal position. The guide opening 74 is of a cross-shape because the first attachment member (42A or 42B) may pass through it when the assembly is installed to the load sensing block 24. The load sensing block 24 also has a ring-shaped cushion 80 attached on the guide plate 70 along its peripheral edge for preventing contact of the load applying block 14 with the guide plate 70 in case that the load applying block 14 exceeds the lower limit position for some reason or another.

The lower portion of the second attachment member (44A or 44B) is received in the receptacle 32, with a sufficient gap left between the under surface of the second attachment member (44A or 44B) and the bottom of the receptacle 32 in order to prevent their collision under ordinary situations. However, in case that an unexpected situation allows such a collision, a cushion layer 76 of a suitable material, such as rubber, is affixed on the bottom of the receptacle 32.

After the assembly composed of the test piece and the test piece attachment set is installed to the load sensing block 24 in this manner, the tensile test can be started. For the tensile test, the human operator of the material testing machine 10 uses the computer 20 to enter required parameters for the tensile test, which may include, for example, a desired speed of the load applying block 14 to be driven, a desired vertical position of the load applying block 14 from which it is released into a free fall, and others. The computer 20 transmits to the actuator controller 18 appropriate command signals CMD in accordance with the parameters entered. The actuator controller 18 responds to the command signals CMD by generating actuator control signals CNT to operate the actuator assembly 16, so as to drive the load applying block 14 in a desired direction at a desired speed and/or to a desired vertical position and/or to produce a desired urging force to be applied by the load applying block 14 to the test piece TP. Thus, by using the test piece attachment set 42A, 44A or 42B, 44B, the material testing machine 10 is capable of tensile tests conducted at various strain rates ranging from relatively low strain rates to relatively high strain rates.

Referring next to FIGS. 6 to 8, a material testing machine arranged and constructed according to a second preferred embodiment of the present invention will be described. The material testing machine of the second embodiment has the same arrangement and structure as the material testing machine 10 of the first embodiment except for some of features of the load applying block 14 and the load sensing block 24. Like components and elements are designated by like reference numerals and will not be described for simplicity; only differences between these embodiments will be described in detail in the following description.

Figure 6A:
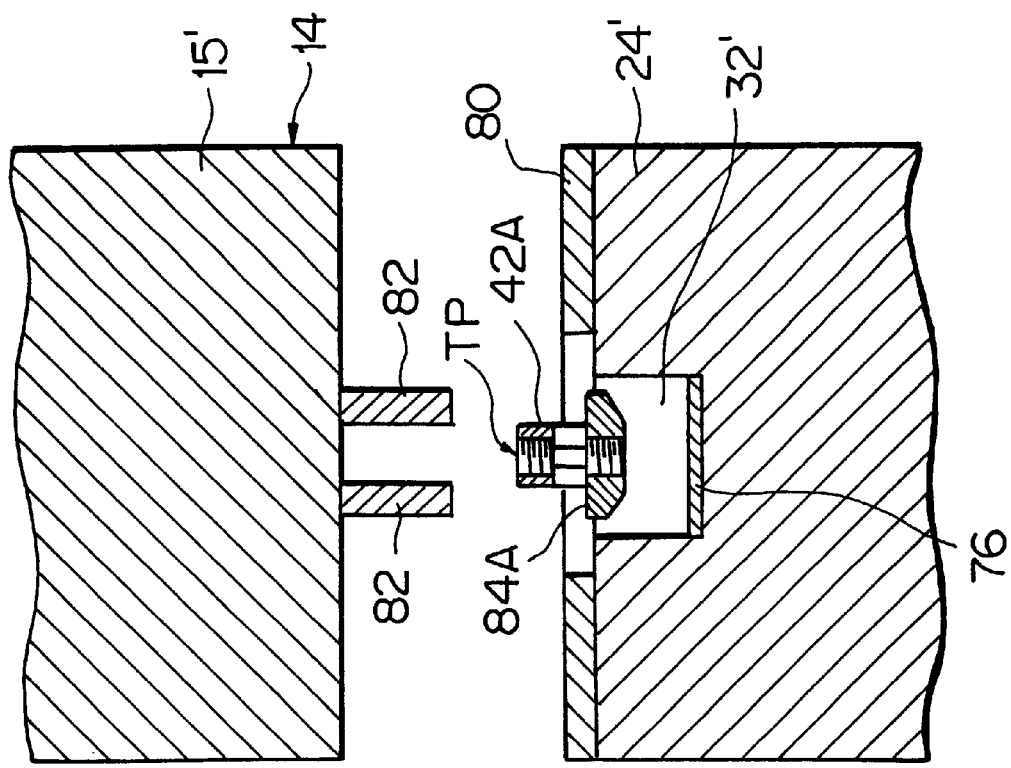
FIGS. 6A and 6B are cross-sectional views showing critical components of a load measuring unit and a load applying unit used in a material testing machine arranged and constructed in accordance with a second embodiment of the present invention.
Figure 6B:
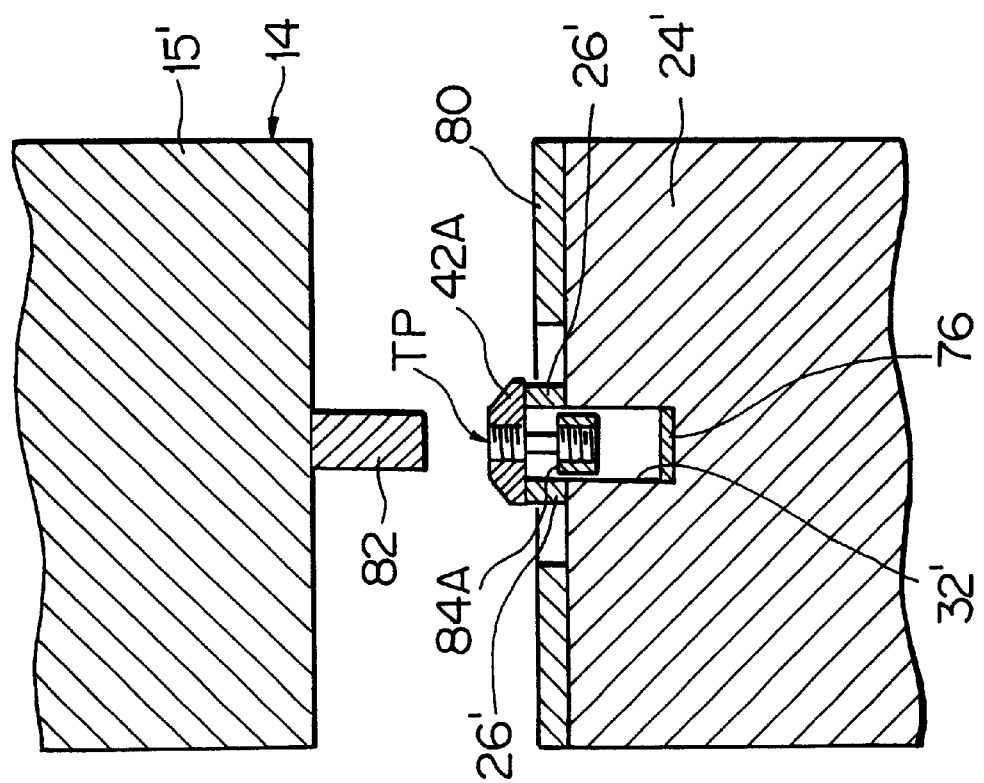

As shown in FIGS. 6A and 6B, the material testing machine of the second embodiment includes a load sensing block 24', which has the same structure as the load sensing block 24 described above, except for the features and arrangement found on the top thereof. Further, the material testing machine of the second embodiment includes a load applying block 14', which has the same structure as the load sensing block 14 described above, except for the features and arrangement found on the bottom thereof. For conducting tensile tests, the material testing machine of the second embodiment uses test piece attachment sets which differ from those used in the machine of the first embodiment.

Specifically, the load sensing block 24' has a receptacle 32' formed in the top surface of the block 24' and at the center of the top surface. The receptacle 32' is of a rectangular shape as viewed in plan. A cushion layer 76 is affixed on the bottom of the receptacle 32'. A pair of sensing projections 26' are provided on the top surface of block 24' and on the opposite sides of the receptacle 32'. The sensing projections 26' have its size and geometry similar to those of the sensing projections 26 described above with reference to FIG. 3 and provides the same functionality as the sensing projections 26. Each sensing projection 26' has four strain gages (not shown) affixed on its side surface at angular intervals of ninety degrees, as with the sensing projections 26. The load sensing block 24' has a ring-shaped cushion layer 80 affixed on the top surface. Further, the load sensing block 24 is provided with a test-piece-strain measuring unit comprising displacement sensors (not shown) for sensing displacement of the lower end of the test piece TP' and determining the strain of the test piece TP' based on the sensed displacement.

The load applying block 14' is a block made of steel and having a volume and a mass both of which are sufficient for the purposes of the load applying block 14'. The load applying block 14' includes a body 15' having a flat bottom surface with a pair of small, rectangular-parallelepiped, load applying projections 82 extruding downward from the bottom surface. Each load applying projection 82 has an axis extending in vertical direction with its upper and lower ends being proximal and distal ends, respectively. Thus, the load applying projections 82 are connected with the body 15' of the load applying block 14' at their proximal ends.

The load applying projections 82 is used to apply a tensile load to a test piece through a test piece attachment set described later. For a tensile test conducted at a very high strain rate, or an impact tensile test, a stress wave is produced in each load applying projection 82 by an impact acting on the distal (lower) end thereof from a test piece attachment connected to the test piece. The stress wave produced may propagate along the longitudinal axis of the load applying projection 82 from the distal end to the proximal end, and a considerable part of the energy of the stress wave reaching the proximal end may further propagate into the body 15' to reach peripheral surfaces of the body 15' and reflect again and again from one peripheral surface to another. This effectively prevents dynamic behavior of the load applying block 14 due to the stress wave from substantially effecting on the impact load applied to the test piece. The cross section of each load applying projection 82 is much smaller than that of the body 15', so that only a negligible portion of the energy of the stress wave in the body 15' may enter again into the load applying projections 82.

The material testing machines according to the first and second embodiments are identically the same in arrangement and structure for the parts and components other than those described above. Accordingly, by using changeable load applying blocks and load sensing blocks, these two embodiments may be realized in a single material testing machine.

FIGS. 7 and 8 show two sets of test piece attachments suitable for use with the material testing machine of the second embodiment. The test piece attachment set of FIG. 7, comprising first and second attachment members 42A and 84A, may be used for a tensile test using a circular-rod-type test piece TPA. The test piece attachment set of FIG. 8, comprising first and second attachment members 42B and 84B, may be used for a tensile test using a flat-strip-type test piece TPB.

For conducting a tensile test, at first, the first attachment member (42A or 42B) and the second attachment member (84A or 84B) are connected to the upper and lower ends of the test piece (TPA or TPB), respectively, to form a test piece/attachment set assembly. The assembly is then disposed in position between the load applying block 14' and the load sensing block 24' with the first (upper) end of the test piece (TPA or TPB) directed toward the load applying block 14' and the second (lower) end toward the load sensing block 24'. As seen from FIGS. 7 and 8, the first attachment members 42A and 42B are the same as those described above with reference to FIGS. 4 and 5.

The second attachment member (84A or 84B) is adapted to receive a load from the distal (lower) ends of the load applying projections 82 of the load applying block 14'. Specifically, the second attachment member 84A of FIG. 7 is an elongated bar-like member made of steel, which extends in horizontal direction when installed to the load sensing block 14'. It has a threaded hole 86 at the center thereof for receiving the lower threaded end of the circular-rod-type test piece TPA. Similarly, the second attachment member 84B of FIG. 8 is an elongated bar-like member made of steel, which extends in horizontal direction when installed to the load sensing block 14'. It has a slit 92 at the center thereof for receiving the lower end of the flat-strip-type test piece TPB and a hole 96 for snugly receiving a pin 94 for securing the end of the test piece TPB to the second attachment member 84B.

Thus, the second attachment member (84A or 84B) is connected at the center thereof to the test piece (TPA or TPB) and receives at opposite ends thereof a load from the distal (lower) ends of the pair of load applying projections 82. The second attachment member (42A or 42B) has a sufficient rigidity so that it is subjected to little bending when receiving the load.

As shown in FIGS. 6A and 6B, with the test piece/attachment set assembly being disposed in position, the first attachment member 42A connected to the upper end of the test piece TPA is placed at its opposite ends on the distal (top) ends of the sensing projections 26', so that the assembly is supported by the sensing projections 26'. The second attachment member 84A is received in the receptacle 32', with a sufficient gap left between the under surface of the second attachment member 84A and the bottom of the receptacle 32' in order to prevent their collision under ordinary situations. However, in case that an unexpected situation allows such a collision, a cushion layer 76 of a suitable material, such as rubber, is affixed on the bottom of the receptacle 32.

For a tensile test using a flat-strip-type test piece, the test piece attachment set of FIG. 8 may be used. In such a case, the assembly composed of the test piece TPB and the test piece attachment set of FIG. 8 may be installed to the material testing machine in the same manner as described above for the assembly of FIG. 7.

After the assembly composed of the test piece and the test piece attachment set is installed to the load sensing block 24' in this manner, the tensile test can be started. For the tensile test, the material testing machine of the second embodiment is operated in the same manner as the material testing machine 10, as described above in detail. In operation, when the load applying block 14' is displaced is downward, the lower ends of the load applying projections 82 come into engagement with the opposite ends of the second attachment member (84A or 84B) and applies a downward load thereto, which is transmitted to the test piece (TPA or TPB) as a tensile load.

The test piece attachment sets of FIGS. 7 and 8 may be suitably used for those tensile tests which use static or quasi-static loads, as well as for those which are conducted at low or moderate strain rates. However, the test piece attachment sets of FIGS. 7 and 8 may be less suitable than the test piece attachment sets of FIGS. 4 and 5 for those tensile tests which are conducted at relatively high strain rates, or impact tensile rates, because the second attachment member (84A or 84B) tends to be snapped away by the load applying projections 82 at impact, so that the measurement may be possibly subjected to relatively large disturbances. On the other hand, in comparison with the attachment sets of FIGS. 4 and 5, the attachment sets of FIGS. 7 and 8 may be advantageously fabricated at lower costs, so that they are more usable for tensile tests conducted at low or moderated strain rates.

Referring next to FIGS. 9 to 13, a material test machine arranged and constructed according to a third preferred embodiment of the present invention will be described. The material testing machine of the third embodiment has the same arrangement and structure as the material testing machine 10 of the first embodiment except for some of features of the load applying block 14 and the load sensing block 24. Like components and elements are designated by like reference numerals and will not be described for simplicity; only differences between these embodiments will be described in detail in the following description.

Figure 9:
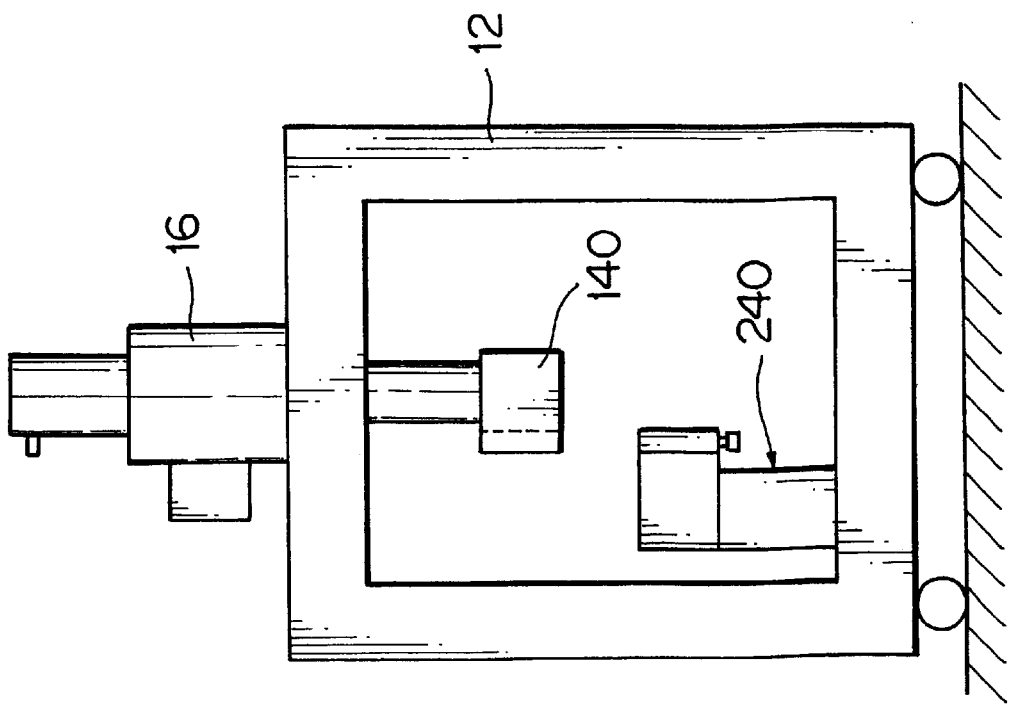
FIG. 9 is a schematic showing a part of a material testing machine arranged and constructed in accordance with a third embodiment of the present invention.
Figure 10:
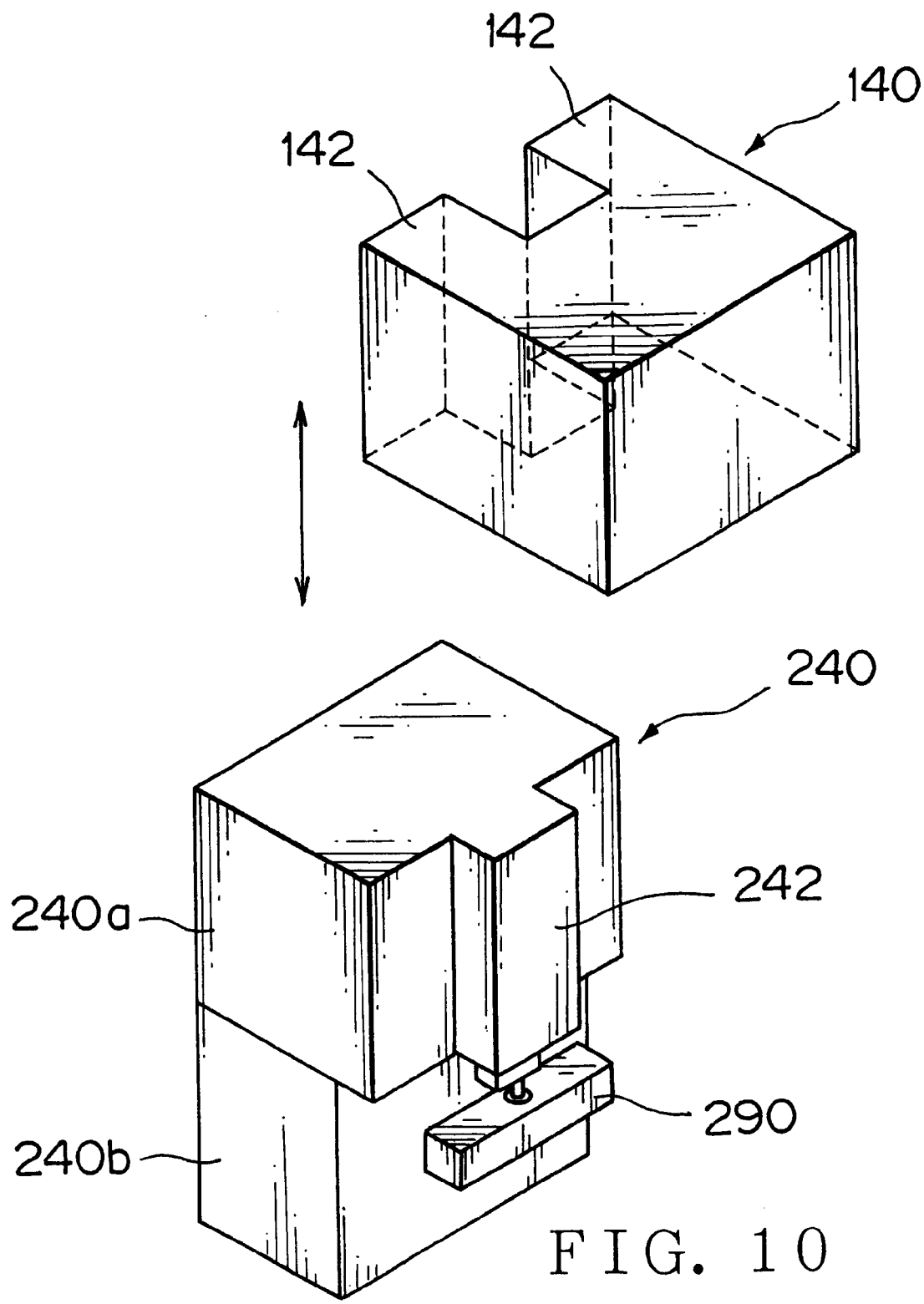
FIG. 10 is a perspective view of a load applying block and a load sensing block used in the material testing machine of FIG. 9 together with a test piece and a test piece attachment for a tensile test, as installed to the load sensing block.

As shown in FIG. 9, the material testing machine of the third embodiment includes a frame 12 and an actuator assembly 16, which are the same as those used in the first embodiment. As shown in FIGS. 9 and 10, the material testing machine of the third embodiment further includes a load applying block 140 and a load sensing block 240. Unlike the load applying block 14 and the load sensing block 24 described above, the load applying block 140 and the load sensing block 240 are offset relative to each other in horizontal direction, such that the load applying block 140 may pass by the load sensing block 240 along one side of the latter when driven in vertical direction.

The load sensing block 140 is a block made of steel and having a volume and a mass both of which are sufficient for the purposes of the load sensing block 240. The load sensing block 240 may be made of any other material which has sufficient toughness and strength for bearing the loads applied to the load sensing block during materials testing, such as phosphor bronze. The load sensing block 240 has a body of a generally rectangular-parallelepiped shape and a side ridge 242 protruding sideward (i.e., in transverse direction with respect to the load-applying (vertical) direction) from one side of the body. The side ridge 242 is a thick ridge extending in vertical direction (i.e., the load-applying direction) and having a fixed, rectangular cross section. The side ridge 242 has a sufficient rigidity for preventing harmful deformation or oscillation when an impact load is applied during an impact test. Insufficient rigidity of the side ridge 242 may possibly affect the resultant measurements of the impact test.

The load applying block 140 has a body of a generally rectangular-parallelepiped shape and a pair of side protrusions 142 protruding sideward (i.e., in transverse direction with respect to the load-applying (vertical) direction) from one side of the body. The side protrusions 142 are thick protrusions having a sufficient rigidity for preventing harmful deformation or oscillation when an impact load is applied during an impact test. Again, any insufficient rigidity of the side protrusions 142 may possibly affect the resultant measurements of the impact test. When the actuator assembly 16 is operated to drive the load applying block 140 in vertical direction, the load applying block 140 passes by the load sensing block 240 along one side of the latter, while the side protrusions 142 of the load applying block 140 pass by the side ridge 242 of the load sensing block 240 close to and along opposite sides of the side ridge 242.

As shown in FIGS. 10 to 14, the load sensing block 240 is composed of upper and lower halves 240a and 240b, which are separately fabricated and thereafter connected into a single block by screws (not shown). The upper and lower halves 240a and 240b each may be fabricated from a single blank of steel by machining it with a milling machine, for example. The separated structure of the load sensing block 204 advantageously reduces the volume of material which has to be removed from the blank in the machining process. It also provides another advantage that good flexibility is obtained by preparing different upper halves for different material tests and/or different test pieces and selecting among them the one suitable for the material test to be conducted and for the test piece to be used. It is appreciated, however, that the present invention is not limited to the use of such separated structure for the load sensing block 240 but may be implemented with a load sensing block having a unitary structure.

Figure 11:
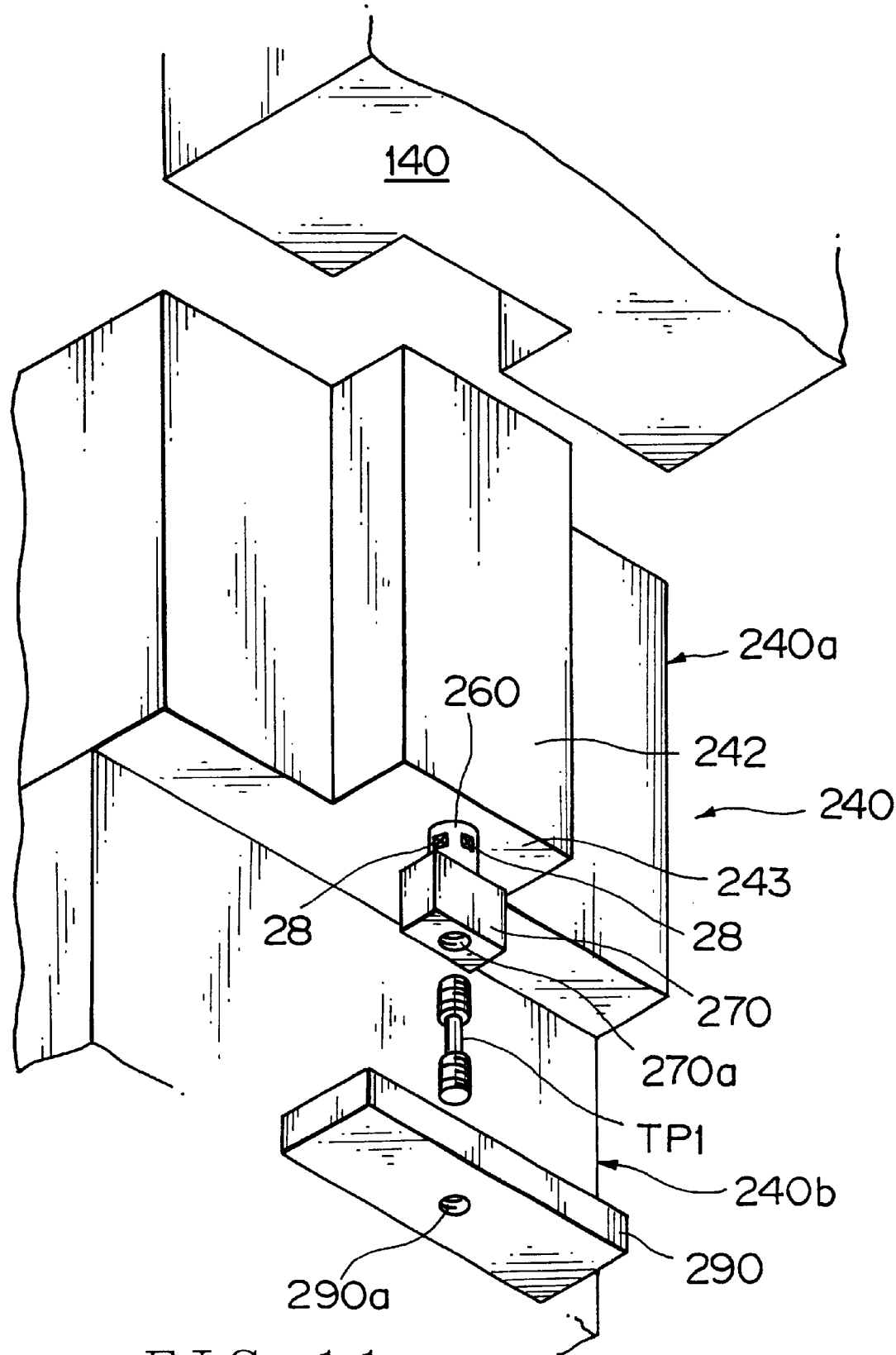
FIG. 11 is a perspective view of an example of a sensing projection of the load sensing block of FIG. 10 together with a circular-rod-type test piece and a test piece attachment for a tensile test, as installed to the sensing projection.
Figure 12:
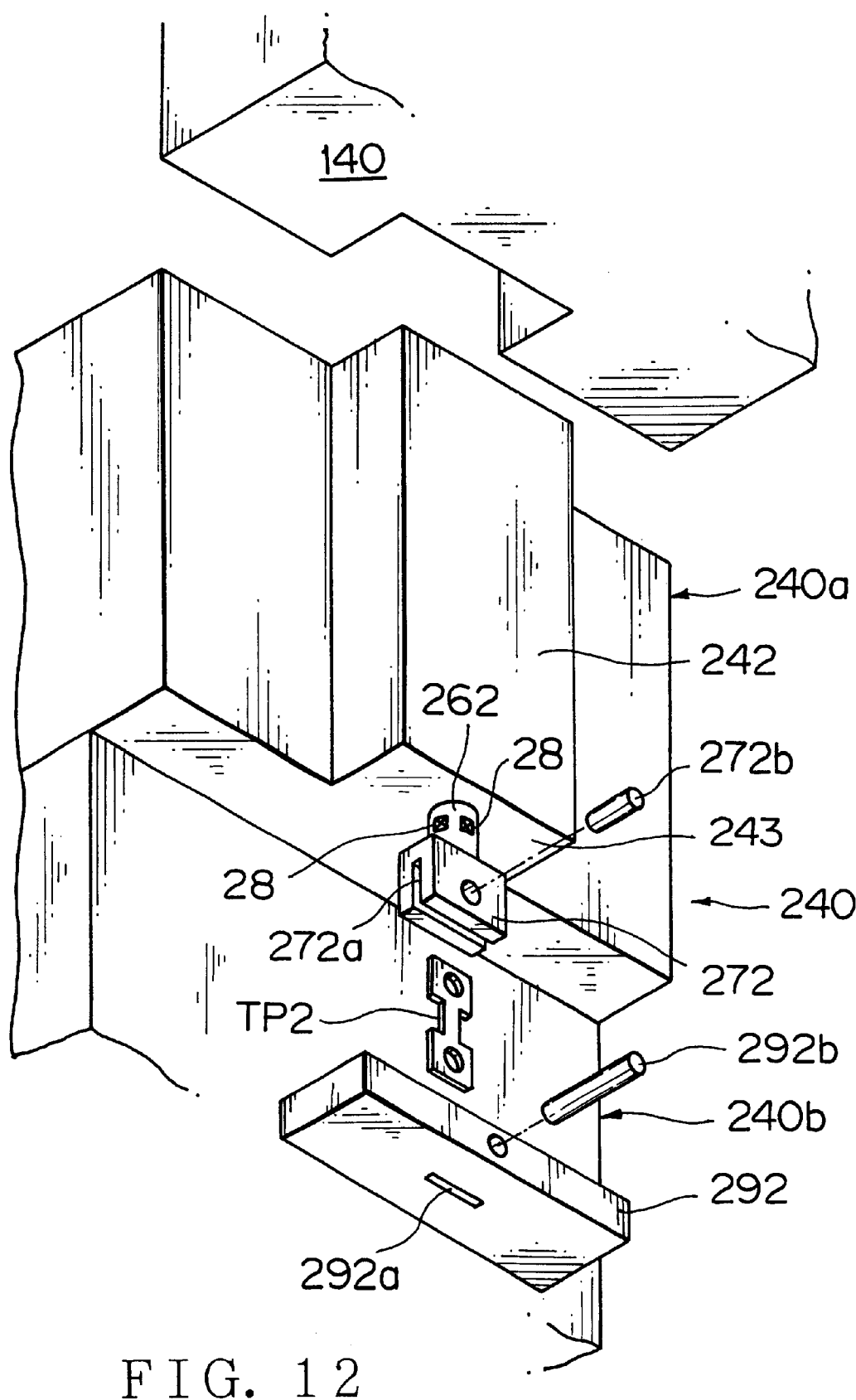
FIG. 12 is a perspective view of another example of a sensing projection of the load sensing block of FIG. 10 together with a flat-strip-type test piece and a test piece attachment for a tensile test, as installed to the load sensing projection.
Figure 13:
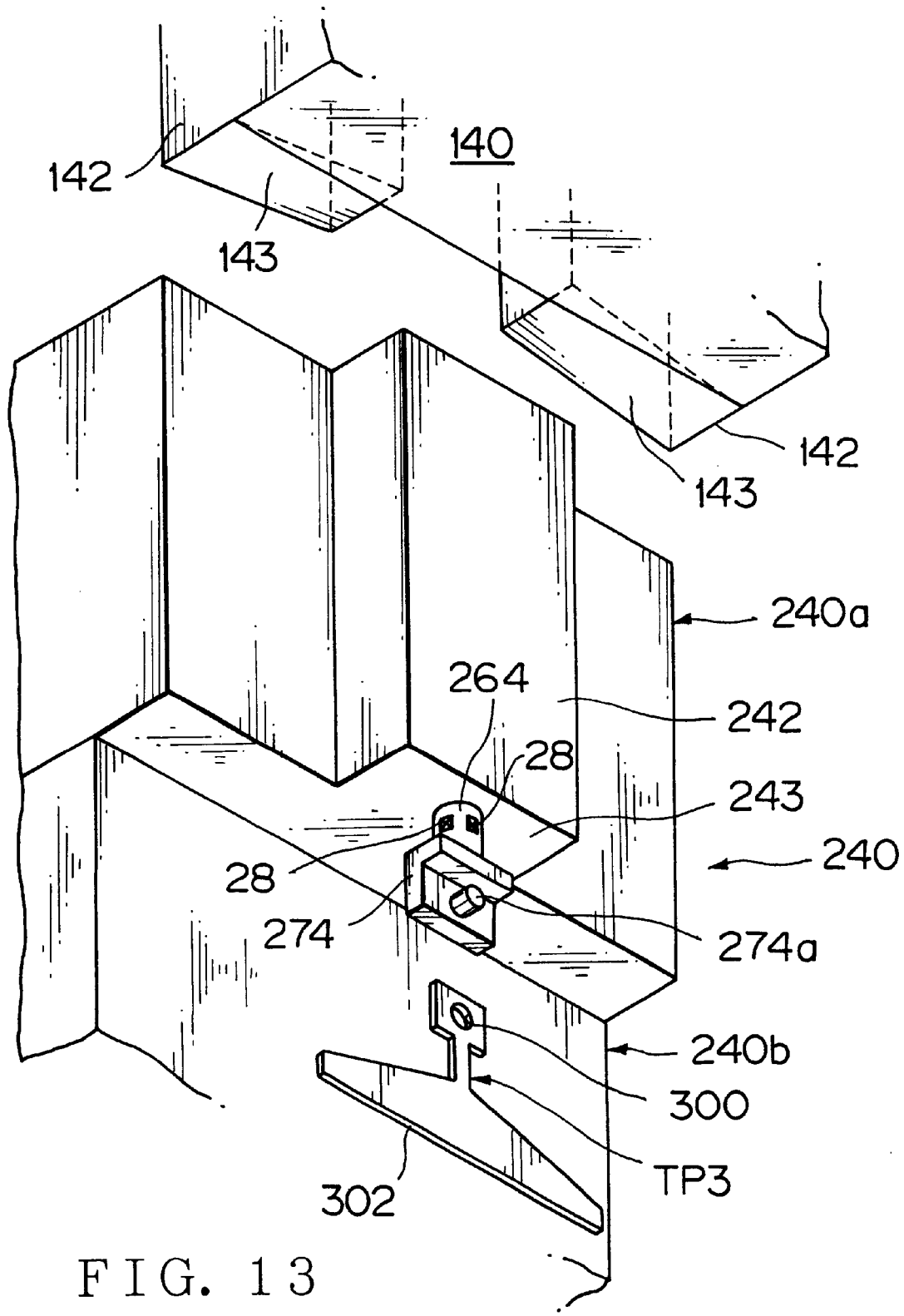
FIG. 13 is a perspective view of a further example of a sensing projection of the load sensing block of FIG. 10 together with a flat-strip-type test piece for a tensile test, as installed to the load sensing projection, and with a modified load applying block.

The side ridge 242 has an end surface (under surface) 243 extending in horizontal direction (i.e., in transverse direction with respect to the load-applying (vertical) direction) and facing downward (see FIGS. 11, 12 and 13). A small, cylindrical, sensing projection is provided such that it projects downward from the under surface 243 and has a connecting portion at the distal (lower) end thereof for connection with the test piece TP. The sensing projection has its size and geometry similar to those of each sensing projection 26 described above with reference to FIG. 3 and provides the same functionality as the sensing projection 26. The sensing projection has four strain gages 28 affixed on its side surface at angular intervals of ninety degrees, as with the sensing projections 26. FIGS. 11, 12 and 13 show three examples of the sensing projection, designated by 260, 262 and 264, respectively, which have different connecting portions 270, 272 and 264 for connecting a test piece to the sensing projection.

The sensing projection (260, 262 or 264) has an axis extending in vertical direction with its upper and lower ends being proximal and distal ends, respectively. Thus, the sensing projection (260, 262 or 264) is connected with the body of the load sensing block 240 at its upper end. The strain gages 28 are electrically connected to an associated signal processing circuitry, as with the first embodiment described above.

While the sensing projection (260, 262 or 264) is formed in a right-circular-cylindrical shape in each example, it may be also formed in a rectangular-parallelepiped shape or others as far as such shape provides no difficulty in measurement using the strain gages affixed on the sensing projection. The size of the sensing projection (260, 262, or 264) is much smaller than that of the body of the load sensing block 240 as well as that of the side ridge 242. Also, the length of the sensing projection (260, 262 or 264) is short enough, as with each sensing projection 26 of FIG. 3, for the reason described above with reference thereto.

The connecting portion (270, 272 or 274) provided at the lower end of the sensing projection (260, 262 or 264) may be formed in a shape suitable for direct connection with a test piece or in a shape suitable for connection with a test piece through a test piece attachment. FIGS. 11, 12 and 13 also show three examples of the connecting portion, which are suitable for particular test pieces differing in geometry as designated by TP1, TP2 and TP3, respectively.

Specifically, the connecting portion 270 of FIG. 11 is capable of direct connection with one end of a circular-rod-type test piece TP1. That is, the connecting portion 270 has a threaded hole 170a with its axis extending in vertical direction, for receiving one threaded end of the test piece TP1. Thus, when installed to the connecting portion 270, the test piece TP1 will have its axis extending in vertical direction, or the load-applying direction.

The connecting portions 272 and 274 of FIGS. 12 and 13, respectively, are capable of direct connection with one end of a flat-strip-type test piece (TP2 or TP3). Specifically, the connecting portion 272 of FIG. 12 has a slit 272a for receiving one end of the test piece TP2 and a hole for snugly receiving a pin 272b for securing the end of the test piece TP2. The connecting portion 274 of FIG. 13 has a plate portion having an L-shaped cross section and a pin 274a projecting in horizontal direction from one side of the L-shaped plate portion. The test piece TP3 has an hole 300 formed in its one end, through which the test piece TP3 is fitted over the pin 274a for connection with the connecting portion 274 of the load sensing block 240. The test pieces TP2 and TP3 have their longitudinal axes extending in vertical direction when installed to the connecting portions 272 and 274, respectively. The test piece TP3 has a novel geometry, which is described in more detail later.

It is preferable that the connecting portion of the sensing projection of the load sensing block 240 is as lightweight as possible for ensuring good measurement results. In terms of this, all of the connecting portions 270, 272 and 274 shown in FIGS. 11, 12 and 13 are desirable examples, among which the connecting portion 274 of FIG. 13 is most desirable.

The upper half 240a of the load sensing block 240 may be fabricated, for example, from a single blank of steel block by machining it with a milling machine, so that the body of the upper half 240a, the side ridge 242, the sensing projection (260, 262 or 264) and the connecting portion (270, 272 or 274) are formed to be completely integral with each other. It is also possible to separately fabricate some of these elements and thereafter connects them into a unitary structure for the upper half 240a through a suitable process, such as welding; however, in such a case, careful consideration has to be made for ensuring good transmission of a stress wave from the sensing projection (260, 262 or 264) to the side ridge 242 and thence to the body of the load sensing block 240, so as to prevent any reflections of the stress wave from affecting the measurement results, as described above with reference to the material testing machine 10 of the first embodiment.

With respect to the arrangement of FIG. 11, for conducting a tensile test, a test piece attachment 290 is connected to the lower end of the test piece TP1. The test piece attachment 290 is an elongated bar-like member made of steel, which extends in horizontal direction when connected to the test piece TP1 which is installed to the load sensing block 240. The test piece attachment 290 has a threaded hole 290a at the center thereof for receiving the lower threaded end of the circular-rod-type test piece TP1.

With respect to the arrangement of FIG. 12, for conducting a tensile test, a test piece attachment 292 is connected to the lower end of the test piece TP2. Again, the test piece attachment 292 is an elongated bar-like member made of steel, which extends in horizontal direction when connected to the test piece TP2 which is installed to the load sensing block 240. The test piece attachment 292 has a slit 292a at the center thereof for receiving the lower end of the flat-strip-type test piece TP2 and a hole for snugly receiving a pin 292b for securing that end of the test piece TP2 to the test piece attachment 292.

The test piece attachments 290 and 292 each has a length greater than the width of the side ridge 242, so that its opposite ends extend out beyond the opposite sides of the side ridge 242. The test piece attachments 290 and 292 each receives a downward load at its opposite ends from the side projections 142 of the load applying block 140 and transmits the load to the test piece (TP1 or TP2), so that the test piece is subjected to a tensile load in vertical direction.

The test piece TP3 of FIG. 13 requires no test piece attachment to be connected to its lower end. The test piece TP3 has an engaging portion 302 formed at its lower end, which is elongated in shape and extends transversely with respect to the longitudinal axis of the test piece TP3. The engaging portion 302 has a length greater than the width of the side ridge 242, so that its opposite ends extend out beyond the opposite sides of the side ridge 242. The engaging portion 302 receives a downward load at its opposite ends from the side projections 142 of the load applying block 140 and transmits the load to the test piece TP3, so that the test piece is subjected to a tensile load in vertical direction.

The upper edges or shoulders of the engaging portion 302, against which the bottom surfaces of the side protrusions 142 of the load applying block 140 come into contact, slant down outwardly at a certain angle (about ten degrees, for example) relative to horizontal direction. The load applying block 140' which is specifically designed for use with the test piece TP3 has the bottom surfaces 143 of the side protrusions 142 slanting at the same angle, as shown in FIG. 13. The test piece TP3 may be modified such that the engaging portion 302 has horizontal upper edges. In such case, the load applying block 140 shown in FIGS. 11 and 12 may be used in place of the load applying block 140' shown in FIG. 13. In most cases, however, an engaging portion having slanting upper edges at an angel up to thirty degrees, and more preferably at an angle between eight to twelve degrees, relative to horizontal direction may effectively suppress any disturbances to the load measurements.

In a typical high-strain-rate test, a material testing machine applies a dynamic load (or load pulse) to a test piece and measures the dynamic load actually applied to the test piece. Where a conventional material testing machine is used to conduct such a high-strain-rate test, disturbances such as oscillations of relatively large magnitude are typically found in the measurements of the dynamic load and, in particular, in the measurements in the initial phase of the load pulse, i.e., in the region of the leading edge of the load pulse. This is one of the major problems encountered in a high-strain-rate tests conducted with a conventional material testing machine and, in particular, in tensile tests conducted at high strain rates. The use of the material testing machine of the third embodiment together with the test piece TP3 of FIG. 13, owing to the novel geometry of the latter, can remedy this problem to a great extent because it require no test piece attachment either for connection with the sensing projection 264 or for receiving the load impulse from the load applying block 140, so that any harmful oscillations and other disturbances will not occur due to such test piece attachments.

The pair of side protrusions 142 of the load applying block 140 serve as engaging portions for engagement with the opposite ends of the test piece attachment (290 or 292) connected to the test piece (TP1 of TP2) or with the opposite ends of the engaging portion 302 of the test piece TP3, in order to apply a lord thereto. As described, when the load applying block 140 is driven to pass by the load sensing block 240 along one side thereof, the side protrusions 142 of the load applying block 140 pass by the side ridge 242 of the load sensing block 240 close to and along opposite sides of the side ridge 242. The test piece attachments 29 and 292 and the engaging portion 302 of the test piece TP3 each has its opposite ends extending beyond the opposite sides of the side ridge 242, so that the side protrusions 142 can engage with them.

In a tensile test using the material testing machine of the third embodiment described with reference to FIGS. 9 to 13, a method may be conducted including the step of providing a test piece for tensile test (such as, test piece TP1, TP2 or TP3) which has first and second ends and an axis and which is adapted to receive a tensile load applied between the first and second ends. It also includes the step of connecting the first end of the test piece to the connecting portion (270, 272 or 274) at the lower end of the sensing projection (260, 262 or 264) with the axis of the test piece extending in the load-applying (vertical) direction. If the test piece requires an attachment to be connected at its second end, then, an appropriate attachment is connected to the second end of the test piece.

Then, in the method, the load applying block 140 is driven in the direction from the first to the second end of the test piece, so that the load applying block 140 may apply a load to the attachment connected to the second end of the test piece (TP1 or TP2) or to the engaging portion at the second end of the test piece TP3. In this manner a desired tensile load may be applied to the test piece to acquire necessary data so as to accomplish the tensile test.

For driving the load applying block 140 or 140', the actuator assembly 16 is controlled in the manner as described above with reference to the material testing machine 10 of the first embodiment. Depending on the control of the actuator assembly 16, it is possible to conduct tensile tests at various strain rates in a wide strain-rate range covering from relatively low strain rates to relatively high strain rates.

The material testing machine of the third embodiment not only shares the advantages of the material testing machines of the first and second embodiments but also enjoys additional advantages. First, because it permits relatively long elongation of the test piece occurring in the tensile test, it is suitably used for the tensile tests not only for metal materials but also for synthetic resins and other materials which provide longer elongation than metal materials. Second, it permits tensile tests using a variety of test pieces differing in geometry and size to a great extent. Third, it provides good accessibility of the test piece since it is exposed on one side of the load sensing block 240, and thereby it provides good workability to facilitate such material tests that require the test piece to be at a given temperature which may be much higher or lower than the room temperature. Finally, the machine also permits load measurement in a tensile test conducted at a high strain rate with only a low level of noise and with accuracy.

The material testing machine of the third embodiment may be used not only for the tensile test but also for various other material tests by using different test pieces with or without test piece attachments. Any material tests other than the tensile test may be conducted according to the following method.

The test piece used with the material testing machine has first and second ends and is adapted for application of a test load between these ends. The first end of the test piece is connected to the connecting portion (270, 272 or 274) of the sensing projection (260, 262 or 264). A test piece attachment is connected to the second end of the test piece if required. The load applying block 140 is driven to apply a load to the test piece attachment or directly to the test piece if it has no test attachment connected thereto.

In this manner, necessary data is acquired for the material test. With the material testing machine of the third embodiment, by using a test piece specifically designed for the shearing test together with a suitable attachment (if required) for the shearing test, such test may be conveniently performed. Similarly, by using a test piece designed for the fracture toughness test, the high-speed punching test, the bending test or any other type of material tests, together with a suitable attachment (if required) for that type of material test, such test may be conveniently performed as well.

For these material test, the control of the actuator assembly 16 may be performed in a manner similar to that for the tensile test described above. Depending on the control of the actuator assembly 16, the material testing machine of the third embodiment permits these material tests at various strain rates in a wide strain-rate range covering from relatively low strain rates to relatively high strain rates.

Figure 14:
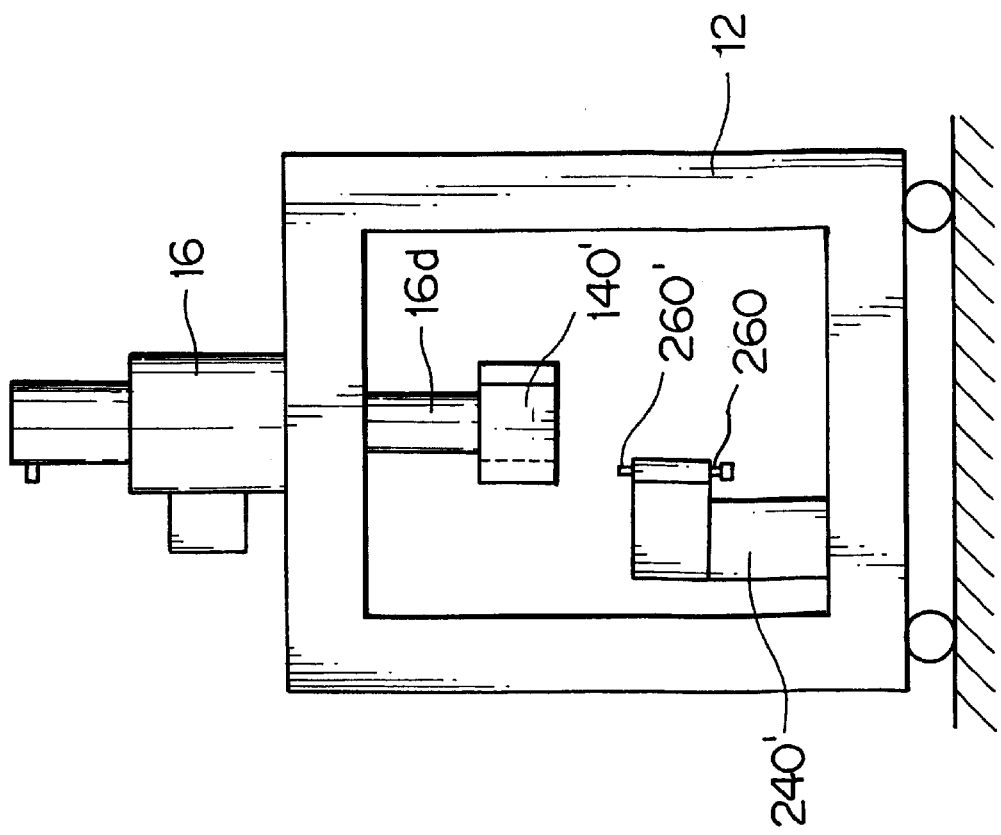
FIG. 14 is a schematic showing a part of a material testing machine arranged and constructed in accordance with a modification of the third embodiment of the present invention.
Figure 15:
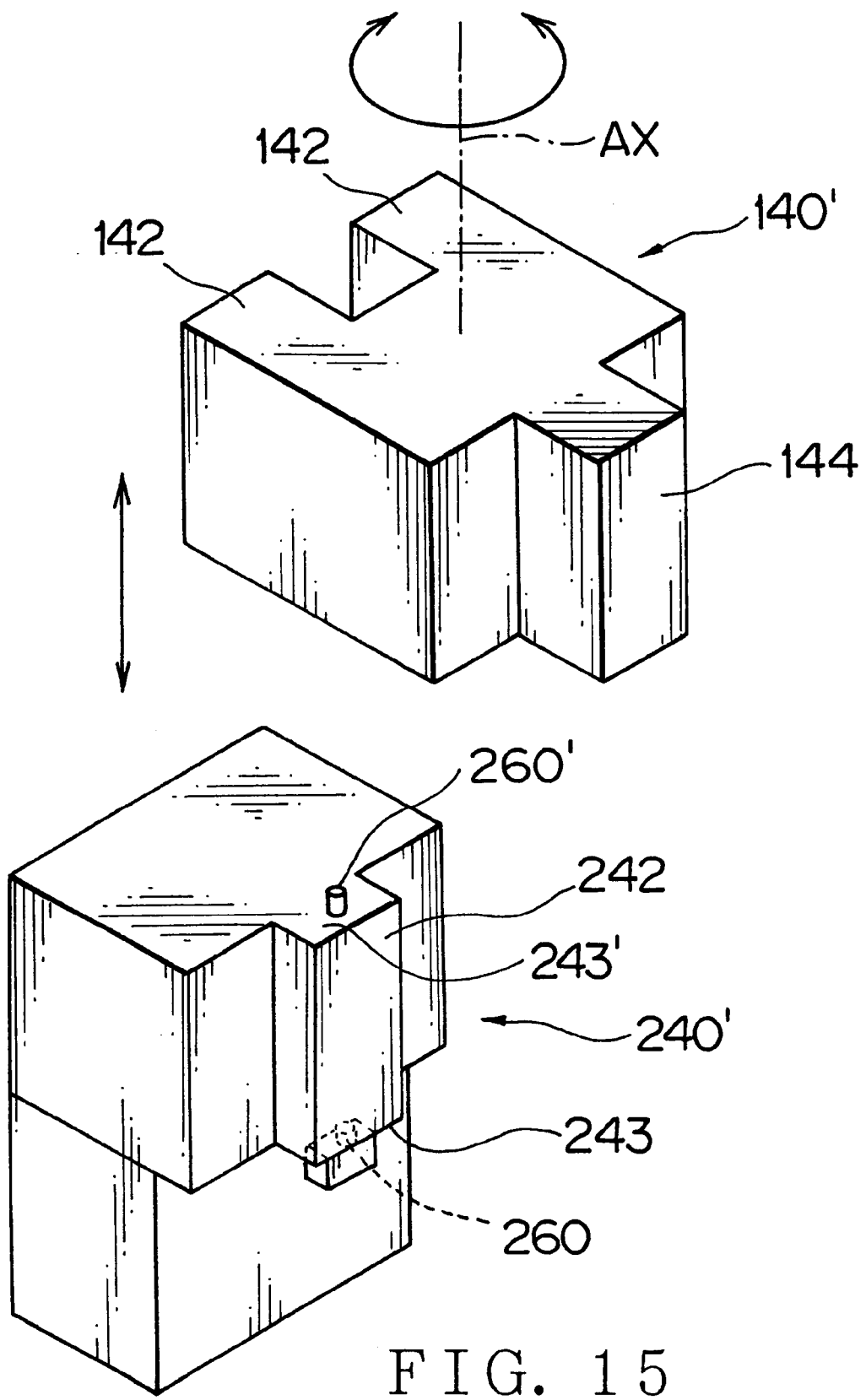
FIG. 15 is a perspective view of a load applying block and a load sensing block used in the material testing machine of FIG. 14.

FIGS. 14 and 15 show a modification of the material testing machine of FIGS. 9 to 13. The material testing machine of FIGS. 14 and 15 has the same arrangement and structure as the material testing machine of the FIGS. 9 to 13 except for some of features of the load applying block 140 and the load sensing block 240. Like components and elements are designated by like reference numerals and will not be described for simplicity. Only differences between the machines will be described in the following description.

The modified machine of FIGS. 14 and 15 includes a load sensing block 240' having a body of a generally rectangular-parallelepiped shape and a side ridge 242 protruding sideward (i.e., in transverse direction with respect to the load-applying (vertical) direction) from one side of the body. The side ridge 242 has the same geometry and size as that used in the load sensing block 240 of FIGS. 9 and 10 and designated by the same reference numeral. The side ridge 242 has opposite end surfaces (upper end surface 243' and lower end surface 243) extending horizontally (i.e., in transverse direction with respect to the load-applying (vertical) direction). A pair of sensing projections 260' and 260 are provided on the end surfaces 243' and 243, respectively. One sensing projection 260 provided on the lower end surface 243 of the side ridge 242 is the same as that used in the load sensing block 240 of FIGS. 9 and 10 and designated by the same reference numeral, i.e., it has the connecting portion at its lower end and four strain gages affixed on its side surface. The other sensing projection 260' provided on the upper end surface 243' of the side ridge 242 is the same as the sensing projection 26 used in the load sensing block 24 of FIG. 3, i.e., it is of a right-circular-cylindrical shape and has four strain gages affixed on its side surface.

The modified machine of FIGS. 14 and 15 includes a load applying block 140', which has the same geometry and size as the load applying block 140 of FIGS. 9 and 10 except for the provision of a third side protrusion 144 protruding sideward in the opposite direction to the pair of side protrusions 142. The load applying block 140' is capable of rotation about the axis AX of the ram rod 16d of the actuator assembly 16 between two angular positions. For providing such rotation, the load applying block 140 may be connected to the ram rod 16d for rotation relative to the latter, and may be manually rotated by the human operator of the machine. Alternatively, the ram rod 16d itself may be supported and guided for rotation about its axis Ax, and an appropriate actuator may be provided for rotating the ram rod 16d together with the load applying block 140'.

When the load applying block 140' is at one angular position shown in FIG. 15, the load applying block 140' and the load sensing block 240' provide the same functionality as the load applying block 140 and the load sensing block 240 of FIGS. 9 and 10, so that they may apply a load to the test piece connected to the lower sensing projection 260. When the load applying block 140' is at the other angular position which is diametrically opposite to the position of FIG. 15, the third side protrusion 144 of the load applying block 140' is just above the upper sensing projection 260', so that the third side protrusion 144 may apply a load to the test piece installed to the upper sensing projection 260'. With the arrangement of FIGS. 14 and 15, the upper sensing projection 260' can be used to conduct a compression test without any test piece attachment, or any other material tests with appropriate test piece attachments. In an alternative arrangement, the load applying block may be formed such that it is capable of connection to the ram rod 16d at two different angular positions. In a further alternative arrangement, two different load applying blocks may be selectively connected to the ram rod 16d and used. These alternative arrangements can provide the same functionality as that described above.

Figure 16A:
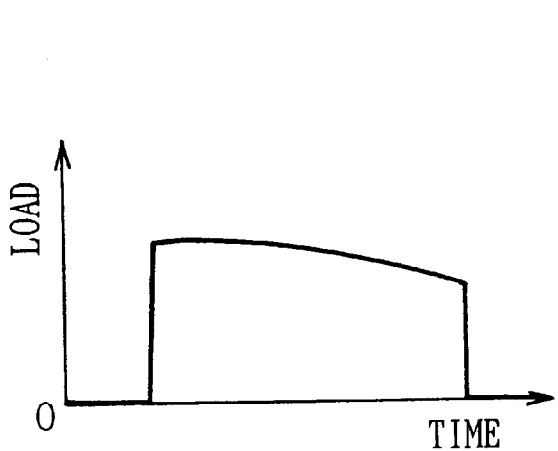
FIGS. 16A to 16C are charts illustrating disturbances found in measured dynamic load waveforms and FIGS. 16D and 16E are charts illustrating nominal stress-strain relationships of test pieces.

As described above, one of the important advantages of the present invention resides in that any disturbances in the dynamic load measurements at the initial phase of a load pulse may be sufficiently suppressed. This is discussed in more detail with reference to FIGS. 16A to 16E. Suppose that a tensile test at a high strain rate is conducted, in which an impact tensile load is applied to a test piece to break the test piece. In such a test, typically, the deformation rate of the test piece is substantially constant throughout the duration of the impact load (or lord pulse). An ideal example of a measured waveform of a load pulse applied to a test piece in such a test is shown in FIG. 16A. As seen, the ideal waveform has a smooth and quickly-rising leading edge, a transition to a plateau with no overshoot, a moderate change in level within the plateau and a smooth and quickly-falling trailing edge at the end of the duration of the lord pulse due to the breakage of the test piece.

Figure 16D:
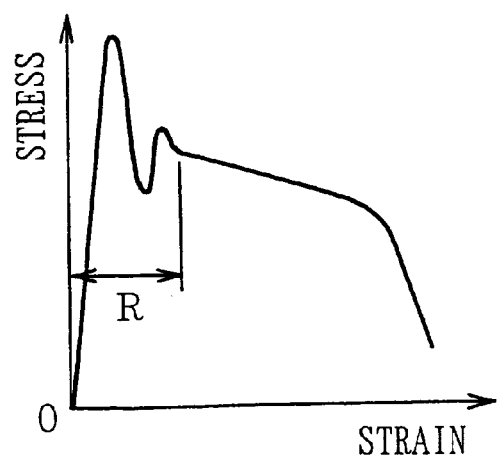
Figure 16B:

When such a test is conducted with a typical, conventional material testing machine, the dynamic load measurement may provide a waveform as depicted in FIG. 16B, in which relatively severe disturbances are found in the initial phase of the load pulse. FIG. 16D depicts the nominal stress-strain relationship of the test piece which is derived from the measurements of the load pulse shown FIG. 16B and associated measurements of the strain of the test piece. As seen from FIG. 16D, those of the measurements which correspond to the region of the initial phase of the load pulse, as marked by a circle R in this figure, provide only low reliability.

Figure 16E:
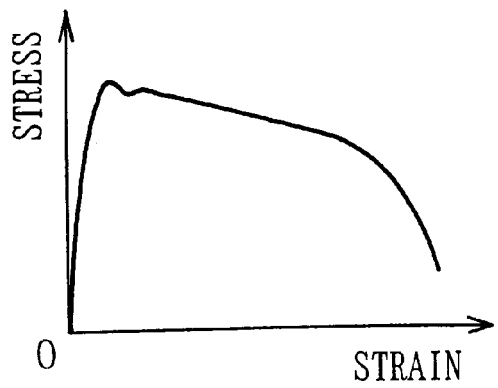
Figure 16C:
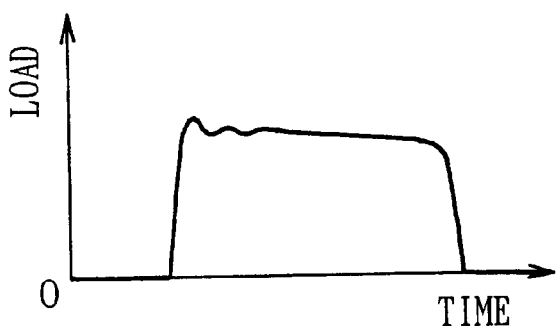

In contrast, when such a test is conducted with a material testing machine in accordance with the present invention, the resultant dynamic load measurements may provide a waveform as depicted in FIG. 16C, which contains only a lower level of noise in the initial phase of the load pulse. The nominal stress-strain relationship, which is derived from the measurements of the load pulse shown FIG. 16C and associated measurements of the strain of the test piece, may provide high reliability throughout the whole range of the relationship as shown in FIG. 16E.

As appreciated from the above description, the material testing machine according to the present invention is usable for material tests conducted at different strain rates in a wide strain-rate range covering from relatively low strain rates to relatively high strain rates, as well as for material tests necessitating relatively large deformation of the test piece. The material testing machine also provides load measurements that contain only a low level of noise even in a high-strain-rate material test conducted at a strain rate of $10^3$/sec. or higher, as well as provide precision measurements throughout the duration of an impact load including the initial phase of the impact load, in which a high level of noise is likely to occur with conventional material testing machines. The material testing machine is also usable for material tests using various test pieces differing in geometry, such as of a circular-rod-type and a flat-strip-type. The material testing machine is also usable, with or without a test piece attachment or a set of test piece attachments if appropriate, for a variety of material tests including compression test, tensile test, shearing test, fracture toughness test and others, which may be conducted at different strain rates in a wide strain-rate range.

Having described the present invention with reference to the preferred embodiments thereof, it is to be understood that the present invention is not limited to the disclosed embodiments, but may be embodied in various other forms without departing from the spirit and the scope of the present invention as defined by the appended claims.

What is claimed is:

1. A material testing machine having a frame, load applying means for applying a load in a predetermined direction to a test piece and load measuring means for sensing a load applied to the test piece, said material testing machine comprising:

(a) said load measuring means comprising a load sensing block having (a-1) a body with sufficient volume and mass and (a-2) at least one sensing projection which is sufficiently smaller than said body of said load sensing block and which has (i) a distal end, (ii) a proximal end connected to said body of said load sensing block, (iii) a longitudinal axis extending in said predetermined direction and (iv) a side surface;

(b) said load measuring means further comprising (b-1) a plurality of strain gages affixed on said side surface of said sensing projection and (b-2) processing means for processing outputs of said strain gages to determine a load acting on said sensing projection;

(c) said load sensing block being arranged such that a stress wave produced in said sensing projection by an impact acting on said distal end of said sensing projection can propagate along said longitudinal axis of said sensing projection from said distal end to said proximal end and that a first part of an energy of the stress wave reaching said proximal end can further propagate into said body of said load sensing block to reach peripheral surfaces of said body and reflect again and again from one peripheral surface to another so that the stress wave in said body will finally decades out to lose dynamic behavior thereof;

(d) said load sensing block being arranged such that a second part of the energy of the stress wave reaching said proximal end can be reflected at said proximal end to return back to said distal end to create shuttling echoes of the stress wave between said distal and proximal ends and that said sensing projection has a sufficiently short length so that said shuttling echoes has a turnaround time sufficiently shorter than a duration of the impact applied to said distal end so as to prevent dynamic behavior of said sensing projection due to the stress wave from substantially effecting on the measurement provided by said load measuring means;

(e) said load measuring means being capable of measurement of static and quasi-static loads with accuracy by using said strain gages to sense any static and quasi-static strains of said sensing projection produced by static and quasi-static loads applied to said distal end of said sensing projection and of measurement of impact loads with accuracy by using said strain gages to sense any dynamic strains of said sensing projection produced by dynamic loads applied to said distal end of said sensing projection;

(f) said load applying means comprising (i) a load applying block, (ii) guide means for guiding said load applying block for movement in said predetermined direction, (iii) drive means for driving said load applying block in said predetermined direction and (iv) control means for controlling said driving means; and (g) said material testing machine being capable of installation of the test piece thereto such that any loads applied by said load applying block to the test piece can be transmitted to said distal end of said sensing projection.

2. A material testing machine according to claim 1, further comprising:

(h) said load applying block having (h-1) a body with sufficient volume and mass and (h-2) at least one load applying projection projecting from said body of said load applying block, said load applying block being arranged such that a stress wave produced in said load applying projection by an impact acting thereon may propagate into said body of said load applying block to reach peripheral surfaces of said body and reflect again and again from one peripheral surface to another, so as to prevent dynamic behavior of said load applying block due to the stress wave from substantially effecting on a load applied to the test piece.

3. A material testing machine according to claim 1, further comprising:

(i) test-piece-strain measuring means for measuring a strain of the test piece produced by a load applied to the test piece.

4. A material testing machine according to claim 1, wherein:

said drive means is capable of accelerating said load applying block to a desired velocity and causing a collision of said load applying block against the test piece to thereby apply an impact load to the test piece, so as to permit material tests at relatively high strain rates.

5. A material testing machine according to claim 4, wherein:

said drive means is capable of displacing said load applying block in said predetermined direction at a controlled, relatively low velocity as controlled by said control means, so as to permit material tests at relatively low strain rates.

6. A material testing machine according to claim 4, wherein:

said control means controls a magnitude of a load, and said drive means is capable of urging said load applying block in said predetermined direction such that the load having a controlled magnitude may be applied by said load applying block to said test piece, so as to permit material tests using static and quasi-static loads.

7. A material testing machine according to claim 5, wherein:

said control means controls a magnitude of a load, and said drive means is capable of urging said load applying block in said predetermined direction such that the load having a controlled magnitude may be applied by said load applying block to said test piece, so as to permit material tests using static and quasi-static loads.

8. A material testing machine according to 1, wherein:

said predetermined direction is vertical direction;

said control means controls a vertical position of said load applying block;

said driving means comprises lift means for lifting up/down said load applying block and position measuring means for measuring vertical position of said load applying block; and said driving means is capable of subjecting said load applying block to a free fall from a controlled vertical position and causing a collision of said load applying block against the test piece to thereby apply an impact load to the test piece, so as to permit material tests at relatively high strain rates.

9. A material testing machine according to claim 8, wherein:

said lift means is capable of lifting up/down said load applying block at a controlled, relatively low velocity as controlled by said control means, so as to permit material tests at relatively low strain rates.

10. A material testing machine according to claim 8, wherein:

said control means controls a magnitude of a load, and said lift means is capable of urging said load applying block in vertical direction such that the load having a controlled magnitude may be applied by said load applying block to said test piece, so as to permit material tests using static and quasi-static loads.

11. A material testing machine according to claim 8, wherein:

said control means controls a magnitude of load, and said lift means is capable of urging said load applying block in vertical direction such that the load having a controlled magnitude may be applied by said load applying block to said test piece, so as to permit material tests using static and quasi-static loads.

12. A material testing machine according to claim 1, wherein:

said predetermined direction is vertical direction;

said load applying block is disposed above said load sensing block;

said load sensing block has a top surface facing said load applying block and having a pair of said sensing projections formed thereon;

said load sensing block has a receptacle formed in said top surface between said pair of sensing projections, for receiving the test piece having test piece attachments connected thereto;

said pair of sensing projections are capable of placement thereon of a test piece attachment connected to the test piece for installation of the test piece to said material testing machine.

13. A material testing machine according to claim 12, wherein:

said load applying block has a bottom surface having a pair of load applying projections; and said load applying projections having respective distal ends capable of contact with another test piece attachment connected to the test piece in order to apply a load to the test piece.

14. A material testing machine according to claim 12, wherein:

said load applying block has a bottom surface having a load applying area defined at the center thereof; and said load applying area is capable of contact with a second test piece attachment connected to the test piece in order to apply a load to the test piece.

15. A material testing machine according to claim 1, wherein:

said load sensing block has a side ridge protruding in transverse direction with respect to said predetermined direction from said body of said load sensing block;

said side ridge has an end surface extending in transverse direction with respect to said predetermined direction;

said load sensing block has said sensing projection provided on said end surface; and said sensing projection has a connecting portion at said distal end thereof for connection with the test piece.

16. A material testing machine according to claim 15, wherein:

said connecting portion of said sensing projection is capable of direct connection with the test piece.

17. A material testing machine according to claim 15, wherein:

said connecting portion of said sensing projection is capable of connection with a test piece attachment which is connected with the test piece, for indirect connection with the test piece.

18. A material testing machine according to claim 15, wherein:

said guide means is so arranged as to guide said load applying block such that said load applying block passes by said load sensing block along one side of said load sensing block and close to said side ridge; and said load applying block has an engaging portion for engagement with a test piece attachment connected to one end of the test piece having the other end thereof connected to said connecting portion of said sensing projection, for applying a load to the test piece.

19. A material testing machine according to claim 15, wherein:

said guide means is so arranged as to guide said load applying block such that said load applying block passes by said load sensing block along one side of said load sensing block and close to said side ridge; and said load applying block has a pair of side protrusions protruding in transverse direction with respect to said predetermined direction from said body of said load applying block, said pair of side protrusions serving as engaging portions for engagement with a test piece attachment connected to one end of the test piece having the other end thereof connected to said connecting portion of said sensing projection, for applying a load to the test piece.

20. A material testing machine according to claim 19, wherein:

said side ridge extends in said predetermined direction and has a substantially fixed cross section and opposite sides;

said guide means is so arranged as to guide said load applying block such that said pair of side protrusions of said load applying block pass by said side ridge close to and along said opposite sides of said side ridge.

21. A material testing machine according to claim 15, wherein:

said guide means is so arranged as to guide said load applying block such that said load applying block passes by said load sensing block along one side of said load sensing block and close to said side ridge; and said load applying block has an engaging portion for engagement with one end of the test piece having another end thereof connected to said connecting portion of said sensing projection, for applying a load to the test piece.

22. A material testing machine according to claim 15, wherein:

said guide means is so arranged as to guide said load applying block such that said load applying block passes by said load sensing block along one side of said load sensing block and close to said side ridge; and said load applying block has a pair of side protrusions protruding in transverse direction with respect to said predetermined direction from said body of said load applying block, said pair of side protrusions serving as engaging portions for engagement with one end of the test piece having another end thereof connected to said connecting portion of said sensing projection, for applying a load to the test piece.

23. A material testing machine according to claim 22, wherein:

said side ridge extends in said predetermined direction and has a substantially fixed cross section and opposite sides;

said guide means is so arranged as to guide said load applying block such that said pair of side protrusions of said load applying block pass by said side ridge close to and along said opposite sides of said side ridge.

24. A material testing machine according to claim 1 wherein:

said load sensing block has a side ridge protruding in transverse direction with respect to said predetermined direction from said body of said load sensing block;

said side ridge has opposite end surfaces extending in transverse direction with respect to said predetermined direction;

said load sensing block has two said sensing projections one provided on each of said opposite end surfaces;

at least one of said sensing projections has a connecting portion at said distal end thereof for connection with the test piece;

said guide means is so arranged as to guide said load applying block such that said load applying block passes by said load sensing block along one side of said load sensing block and close to said side ridge; and said load applying block has an engaging portion for engagement with a test piece attachment connected to one end of the test piece having another end thereof connected to said connecting portion of said sensing projection, for applying a load to the test piece.

25. A material testing machine according to claim 1, wherein:

said load sensing block has a side ridge protruding in transverse direction with respect to said predetermined direction from said body of said load sensing block;

said side ridge has opposite end surfaces extending in transverse direction with respect to said predetermined direction;

said load sensing block has two said sensing projections one provided on each of said opposite end surfaces;

at least one of said sensing projections has a connecting portion at said distal end thereof for connection with the test piece;

said guide means is so arranged as to guide said load applying block such that said load applying block passes by said load sensing block along one side of said load sensing block and close to said side ridge; and said load applying block has a pair of side protrusions protruding in transverse direction with respect to said predetermined direction from said body of said load applying block, said pair of side protrusions serving as engaging portions for engagement with a test piece attachment connected to one end of the test piece having another end thereof connected to said connecting portion of said sensing projection, for applying a load to the test piece.

26. A material testing machine according to claim 25, wherein:

said side ridge extends in said predetermined direction and has a substantially fixed cross section and opposite sides;

said guide means is so arranged as to guide said load applying block such that said pair of side protrusions of said load applying block pass by said side ridge close to and along said opposite sides of said side ridge.

27. A material testing machine according to claim 1, wherein:

said load sensing block has a side ridge protruding in transverse direction with respect to said predetermined direction from said body of said load sensing block;

said side ridge has opposite end surfaces extending in transverse direction with respect to said predetermined direction;

said load sensing block has two said sensing projections one provided on each of said opposite end surfaces;

at least one of said sensing projections has a connecting portion at said distal end thereof for connection with the test piece;

said guide means is so arranged as to guide said load applying block such that said load applying block passes by said load sensing block along one side of said load sensing block and close to said side ridge; and said load applying block has an engaging portion of engagement with one end of the test piece having another end thereof connected to said connecting portion of said sensing projection, for applying a load to the test piece.

28. A material testing machine according to claim 1, wherein:

said load sensing block has a side ridge protruding in transverse direction with respect to said predetermined direction from said body of said load sensing block;

said side ridge has opposite end surfaces extending in transverse direction with respect to said predetermined direction;

said load sensing block has two said sensing projections one provided on each of said opposite end surfaces;

at least one of said sensing projections has a connecting portion at said distal end thereof for connection with the test piece;

said guide means is so arranged at to guide said load applying block such that said load applying block passes by said load sensing block along one side of said load sensing block and close to said side ridge; and said load applying block has a pair of side protrusions protruding in transverse direction with respect to said predetermined direction from said body of said load applying block, said pair of side protrusions serving as engaging portions for engagement with one end of the test piece having the other end thereof connected to said connecting portion of said sensing projection, for applying a load to the test piece.

29. A material testing machine according to claim 28, wherein:

said side ridge extends in said predetermined direction and has a substantially fixed cross section and opposite sides;

said means is so arranged as to guide said load applying block such that said pair of side protrusions of said load applying block pass by said side ridge close to and along said opposite sides of said side ridge.

30. A material testing machine according to claim 1, wherein:

said predetermined direction is vertical direction;

said load sensing block has a side ridge protruding in transverse direction with respect to vertical direction from said body of said load sensing block;

said side ridge has an end surface extending in transverse direction with respect to vertical direction and facing downward;

said load sensing block has said sensing projection provided on said end surface;

said distal end of said sensing projection facing downward; and said sensing projection has a connecting portion at said distal end thereof for connection with the test piece.

31. A material testing machine according to claim 30, wherein:

said connecting portion of said sensing projection is capable of direct connection with the test piece.

32. A material testing machine according to claim 30, wherein:

said connecting portion of said sensing projection is capable of connection with a test piece attachment which is connected with the test piece, for indirect connection with the test piece.

33. A material testing machine according to claim 30, wherein:

said guide means is so arranged as to guide said load applying block such that said load applying block passes by said load sensing block along one side of said load sensing block and close to said side ridge; and said load applying block has an engaging portion for engagement with a test piece attachment connected to one end of the test piece having another end thereof connected to said connecting portion of said sensing projection, for applying a load to the test piece.

34. A material testing machine according to claim 30, wherein:

said guide means is so arranged as to guide said load applying block such that said load applying block passes by said load sensing block along one side of said load sensing block and close to said side ridge; and said load applying block has a pair of side protrusions protruding in transverse direction with respect to vertical direction from said body of said load applying block, said pair of side protrusions serving as engaging portions for engagement with a test piece attachment connected to one end of the test piece having the other end thereof connected to said connecting portion of said sensing projection, for applying a load to the test piece.

35. A material testing machine according to claim 34, wherein:

said side ridge extends in vertical direction and has a substantially fixed cross section and opposite sides;

said guide means is so arranged as to guide said load applying block such that said pair of side protrusions of said load applying block pass by said side ridge close to and along said opposite sides of said side ridge.

36. A material testing machine according to claim 30, wherein:

said guide means is so arranged as to guide said load applying block such that said load applying block passes by said load sensing block along one side of said load sensing block and close to said side ridge; and said load applying block has an engaging portion for engagement with one end of the test piece having the other end thereof connected to said connecting portion of said sensing projection, for applying a load to the test piece.

37. A material testing machine according to claim 30, wherein:

said guide means is so arranged as to guide said load applying block such that said load applying block passes by said load sensing block along one said of said load sensing block and close to said side ridge; and said load applying block has a pair of side protrusions protruding in transverse direction with respect to vertical direction from said body of said load applying block, said pair of side protrusions serving as engaging portions for engagement with one end of the test piece having another end thereof connected to said connecting portion of said sensing projection, for applying a lead to the test piece.

38. A material testing machine according to claim 37, wherein:

said side ridge extends in vertical direction and has a substantially fixed cross section and opposite sides;

said guide means is so arranged as to guide said load applying block such that said pair of side protrusions of said load applying block pass by said side ridge close to and along said opposite sides of said side ridge.

39. A material testing machine according to claim 30, wherein:

said driving means comprises lift means for lifting up/down said load applying block and position measuring means for measuring vertical position of said load applying block;

said driving means is capable of subjecting said load applying block to a free fall from a controlled vertical position as controlled by said control means and causing a collision of said load applying block against the test piece to thereby apply an impact load to the test piece, so as to permit material tests at relatively high strain rates.

40. A material testing machine according to claim 39, wherein:

said lift means is capable of lifting up/down said load applying block at a controlled, relatively low velocity as controlled by said control means, so as to permit material tests at relatively low strain rates.

41. A material testing machine according to claim 39, wherein;

said lift means is capable of urging said load applying block in vertical direction such that a load of a controlled magnitude as controlled by said control means may be applied by said load applying block to said test piece, so as to permit material tests using static and quasi-static loads.

42. A test piece attachment set used for installation of a test piece to a material testing machine according to claim 12 for conducting a tensile test, the test piece having first and second ends to be directed toward said load applying block and said load sensing block, respectively, when the test piece is installed to said material testing machine, said test piece attachment set comprising:

(a) first and second test piece attachments for connection to said first and second end of the test piece, respectively;

(b) said first test piece attachment being adapted for placement on said distal ends of said pair of sensing projections while connected to said first end of the test piece; and (c) said second test piece attachment being adapted for engagement with said load applying block while connected to said second end of the test piece;

(d) wherein application of a compressive load by said load applying block to said second test piece attachment results in application of a tensile load between said first and second ends of the test piece.

43. A test piece attachment set according to claim 42, wherein:

said first test piece attachment comprises an elongated bar-like member having a connecting portion at a center thereof for connection to said first end of the test piece.

44. A test piece attachment set used for installation of a test piece to a material testing machine according to claim 13 for conducting a tensile test, the test piece having first and second ends to be directed toward said load applying block and said load sensing block, respectively, when the test piece is installed to said material testing machine, said test piece attachment set comprising:
(a) first and second test piece attachments for connection to said first and second end of the test piece, respectively;
(b) said first test piece attachment being adapted for placement on said distal ends of said pair of sensing projections while connected to said first end of the test piece;
(c) said second test piece attachment being adapted for engagement with said load applying block while connected to said second end of the test piece;
(d) said first test piece attachment comprising an elongated bar-like member having opposite ends adapted for placement on said distal ends of said pair of sensing projections and a connecting portion at a center thereof for connection to said first end of the test piece; and
(e) said second test piece attachment comprising an elongated bar-like member having opposite ends adapted for engagement with said distal ends of said pair of load applying projections to receive a load therefrom and a connecting portion at the center thereof for connection to said second end of the test piece;
(f) wherein application of a compressive load by said load applying block to said second test piece attachment results in application of a tensile load between said first and second ends of the test piece.

45. A test piece attachment set used for installation of a test piece to a material testing machine according to claim 14 for conducting a tensile test, the test piece having first and second ends to be directed toward said load applying bock and said load sensing block, respectively, when the test piece is installed to said material testing machine, said test piece attachment set comprising:
(a) first and second test piece attachments for connection to said first and second end of the test piece, respectively;
(b) said first test piece attachment being adapted for placement on said distal ends of said pair of sensing projections while connected to said first end of the test piece;
(c) said second test piece attachment being adapted for engagement with said load applying block while connected to said second end of the test piece;
(d) said first test piece attachment comprising an elongated bar-like member having opposite ends adapted for placement on said distal ends of said pair of sensing projections and a connecting portion at a center thereof for connection to said first end of the test piece; and
(e) said second test piece attachment comprising a rectangular ring-shaped member having an upper side adapted for engagement with said load applying area of said load applying block to receive a load therefrom and a lower side with a connecting portion at the center thereof for connection to said second end of the test piece;
(f) wherein application of a compressive load by said load applying block to said second test piece attachment results in application of a tensile load between said first and second ends of the test piece.

46. A test piece attachment set according to claim 45, wherein:
said upper side of said second test piece attachment has a top surface on which a cushion layer is affixed to receive a load from said load applying area of said load applying block.

47. A method of conducting a material test with a material testing machine according to claim 15, comprising the steps of:
(a) providing a test piece having first and second ends and an axis and being adapted for a tensile test conducted with a tensile load applied along said axis between said first and second ends;
(b) connecting said first end of said test piece to said connecting portion at said distal end of said sensing projection, such that said axis extends in said predetermined direction;
(c) connecting said second end of said test piece to a test piece attachment; and
(d) driving said load applying block in direction from said first end to said second end of said test piece, so as to apply a load from said load applying block to said test piece attachment connected to said second end of said test piece.

48. The method according to claim 47, wherein:
said step of driving said load applying block comprises driving said load applying block at a velocity that produces a strain of said test piece at relatively high strain rate.

49. The method according to claim 47, wherein:
said step of driving said load applying block comprises driving said load applying block at a velocity that produces a strain of said test piece at relatively low strain rate.

50. A method of conducting a material test with a material testing machine according to claim 15, comprising the steps of:
(a) providing a test piece having first and second connecting portions and being adapted for a material test conducted with a load applied between said first and second ends;
(b) connecting said first connecting portion of said test piece to said connecting portion at said distal end of said sensing projection;
(c) connecting said second end of said test piece to a test piece attachment; and
(d) driving said load applying block so as to apply a load from said load applying block to said test piece attachment connected to said second end of said test piece.

51. The method according to claim 50, wherein:
said step of driving said load applying block comprises driving said load applying block at a velocity that produces a strain of said test piece at relatively high strain rate.

52. The method according to claim 50, wherein:
said step of driving said load applying block comprises driving said load applying block at a velocity that produces a strain of said test piece at relatively low strain rate.

53. A method of conducting a material test with a material testing machine according to claim 15, comprising the steps of:
(a) providing a test piece having first and second ends, said test piece further having a connecting portion and an engaging portion at said first end second ends, respectively, said test piece being adapted for a material test conducted with a load applied between said connecting portion and said engaging portion;

(b) connecting said connecting portion of said test piece to said connecting portion at said distal end of said sensing projection;

(c) driving said load applying block so as to apply a load from said load applying block to engaging portion of said test piece.

54. The method according to claim 53, wherein:
said step of driving said load applying block comprises driving said load applying block at a velocity that produces a strain of said test piece at relatively high strain rate.

55. The method according to claim 53, wherein:
said step of driving said load applying block comprises driving said load applying block at a velocity that produces a strain of said test piece at relatively low strain rate.

* * * * *